(12) United States Patent
Fujimoto et al.

(10) Patent No.: US 12,226,106 B2
(45) Date of Patent: Feb. 18, 2025

(54) APPLICATOR, MEDICAL APPARATUS, AND OPERATION METHOD OF MEDICAL APPARATUS

(71) Applicant: OLYMPUS CORPORATION, Hachioji (JP)

(72) Inventors: Yasuyuki Fujimoto, Hino (JP); Kensuke Uesaka, Hino (JP)

(73) Assignee: OLYMPUS CORPORATION, Tokyo (JP)

( * ) Notice: Subject to any disclaimer, the term of this patent is extended or adjusted under 35 U.S.C. 154(b) by 877 days.

(21) Appl. No.: 17/344,072

(22) Filed: Jun. 10, 2021

(65) Prior Publication Data

US 2021/0298759 A1    Sep. 30, 2021

Related U.S. Application Data

(63) Continuation of application No. PCT/JP2018/046121, filed on Dec. 14, 2018.

(51) Int. Cl.
*A61B 17/128* (2006.01)
*A61B 17/122* (2006.01)

(52) U.S. Cl.
CPC .......... *A61B 17/128* (2013.01); *A61B 17/122* (2013.01)

(58) Field of Classification Search
CPC . A61B 17/128; A61B 17/122; A61B 17/1285; A61B 17/1227
See application file for complete search history.

(56) References Cited

U.S. PATENT DOCUMENTS

| 6,210,398 B1 * | 4/2001 | Ouchi | A61B 17/2909 |
| | | | 600/184 |
| 2003/0083677 A1 * | 5/2003 | Damarati | A61B 17/122 |
| | | | 606/151 |

(Continued)

FOREIGN PATENT DOCUMENTS

| CN | 1953712 A | 4/2007 |
| EP | 1820457 A1 | 8/2007 |
| JP | H11-332870 A | 12/1999 |

(Continued)

OTHER PUBLICATIONS

Mar. 12, 2019 International Search Report issued in International Patent Application No. PCT/JP2018/046121.

(Continued)

*Primary Examiner* — Katherine M Rodjom
(74) *Attorney, Agent, or Firm* — Oliff PLC

(57) ABSTRACT

An applicator capable of operating a clip unit including a first link, a medical apparatus including the applicator and the clip unit, and a method for operating the medical apparatus are disclosed. The applicator includes: a second link capable of engaging with the first link; an operation wire; a sheath capable of accommodating the second link; a slider that is connected to the operation wire and can be operated to move the second link; and a knob. In a state where the slider is in an advanced-most position, the knob can be operated to adjust the length of the wire extending from the slider to the second link between: a first length at which the second link protrudes from the sheath, and a second length that is shorter than the first length, and at which the second link is inside the sheath.

14 Claims, 28 Drawing Sheets

(56) References Cited

U.S. PATENT DOCUMENTS

2005/0143767 A1* 6/2005 Kimura ............... A61B 50/30
606/158
2016/0206853 A1* 7/2016 Bolduc ............. A61M 25/0136

FOREIGN PATENT DOCUMENTS

| | | |
|---|---|---|
| JP | 2006-158668 A | 6/2006 |
| JP | 2007-244826 A | 9/2007 |
| JP | 2010-081970 A | 4/2010 |
| JP | 2012-200518 A | 10/2012 |
| JP | 2015-149997 A | 8/2015 |
| WO | 2018/011846 A1 | 1/2018 |

OTHER PUBLICATIONS

Oct. 7, 2023 Office Action issued in Chinese Patent Application No. 201880100067.9.

* cited by examiner

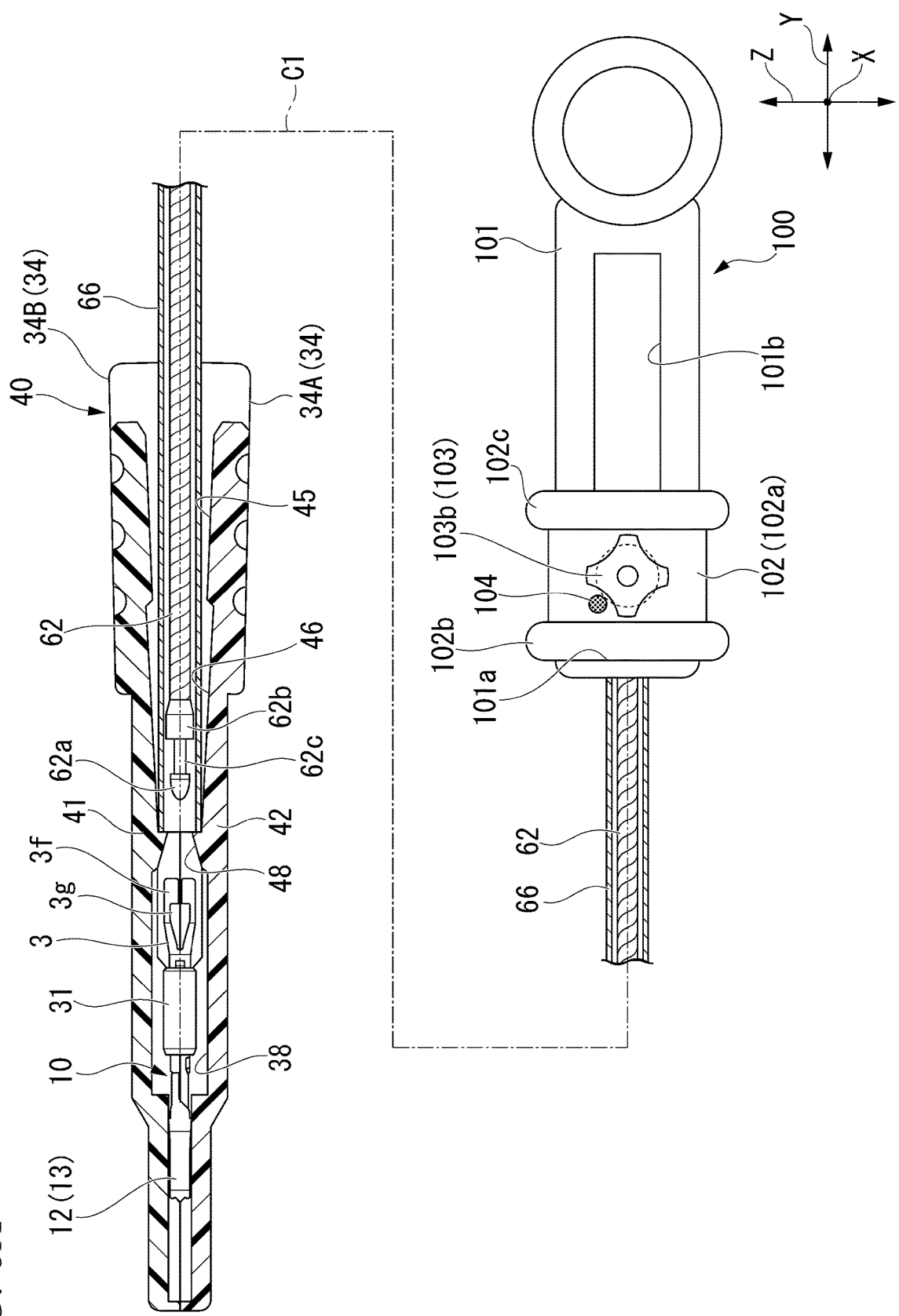

FIG. 6B
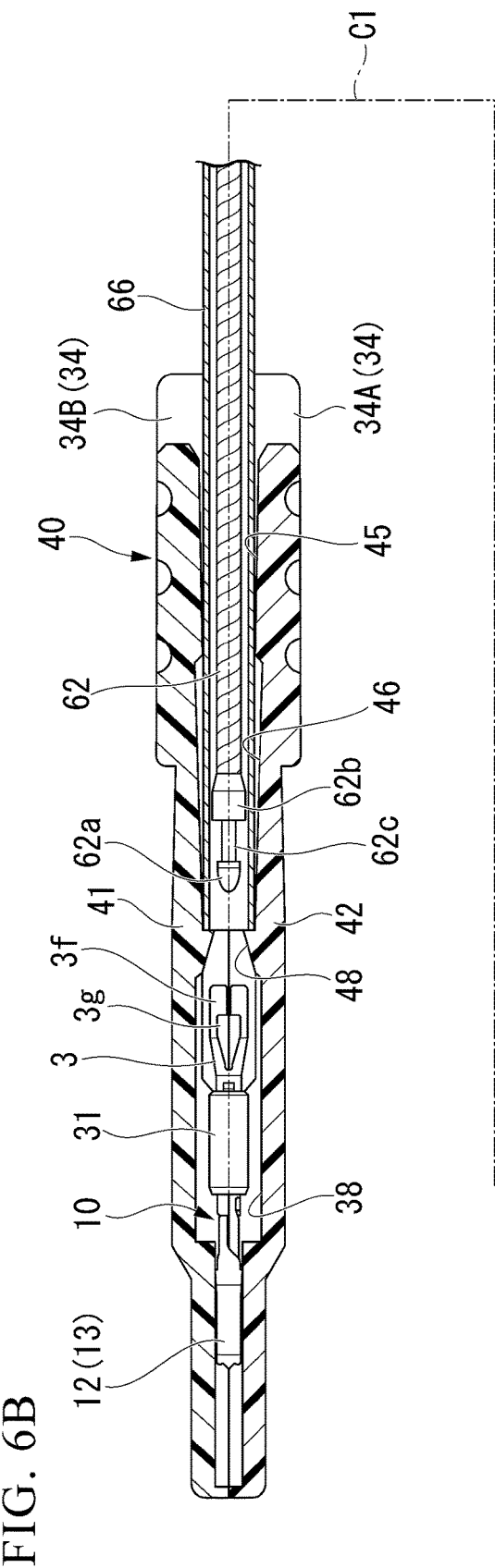
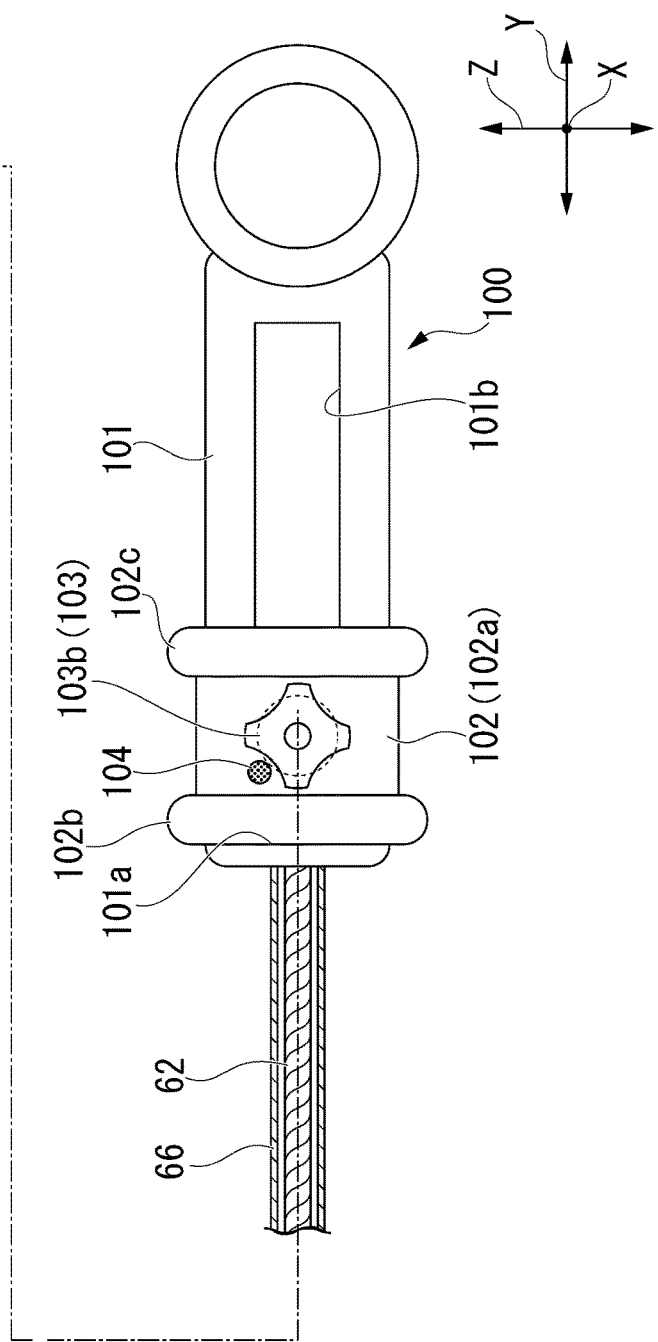

FIG. 6C
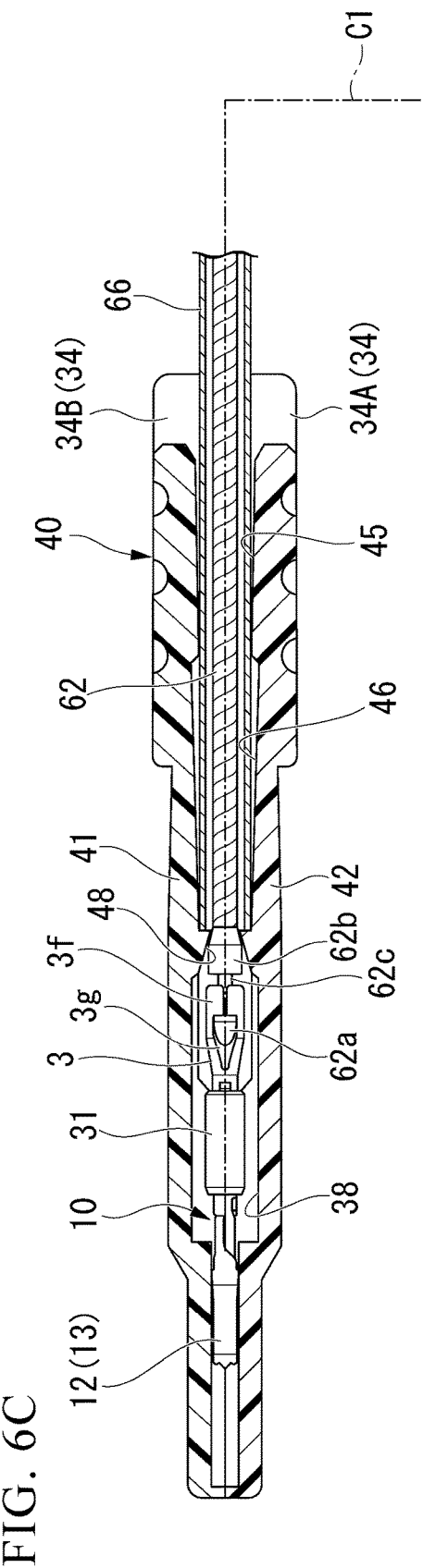
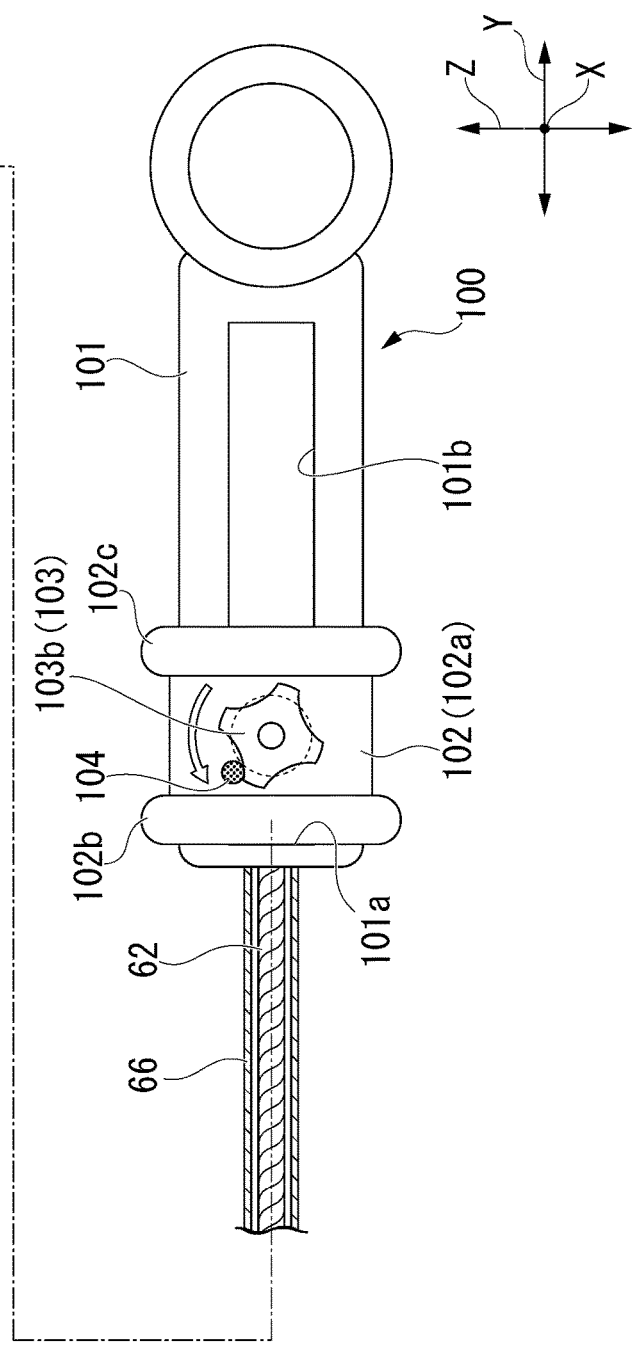

FIG. 6E
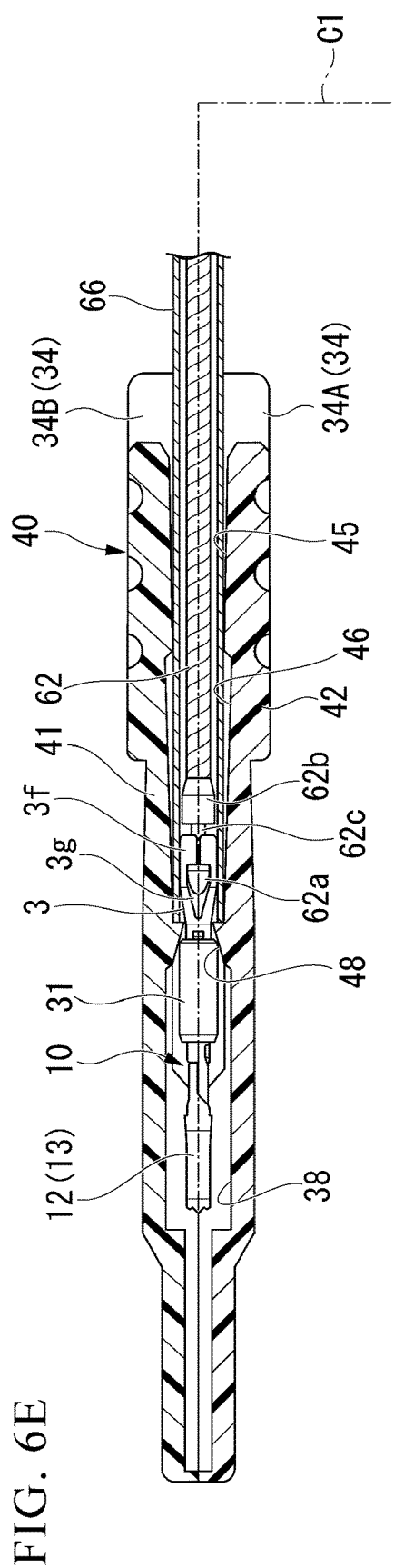
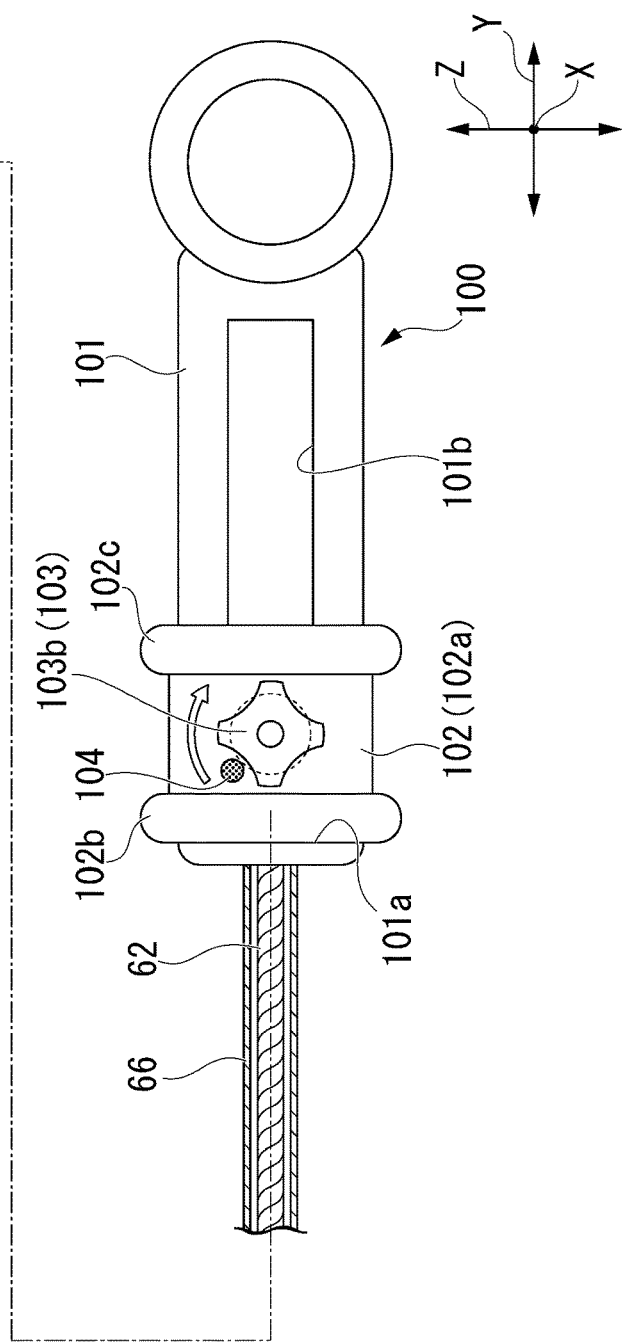

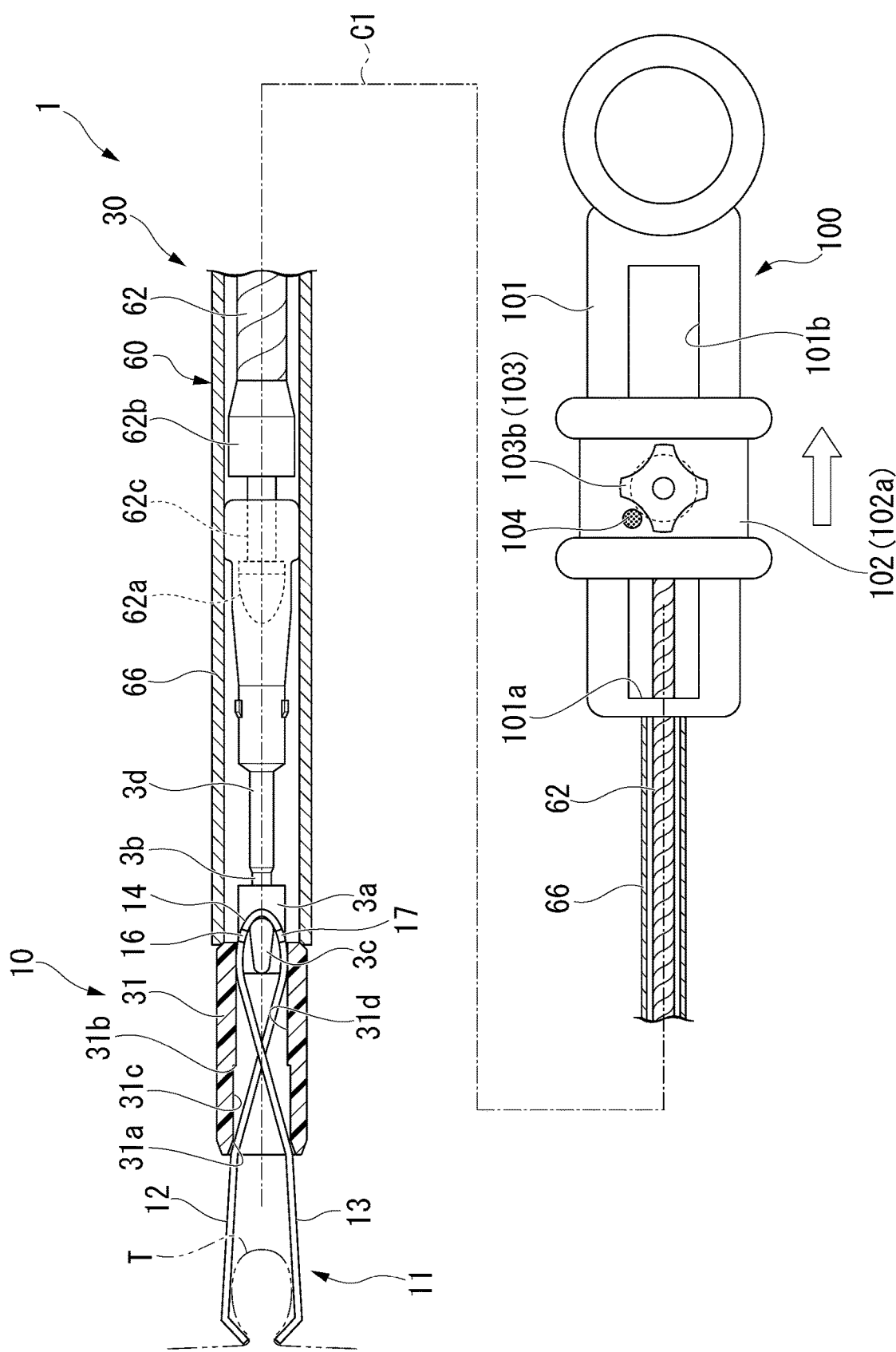

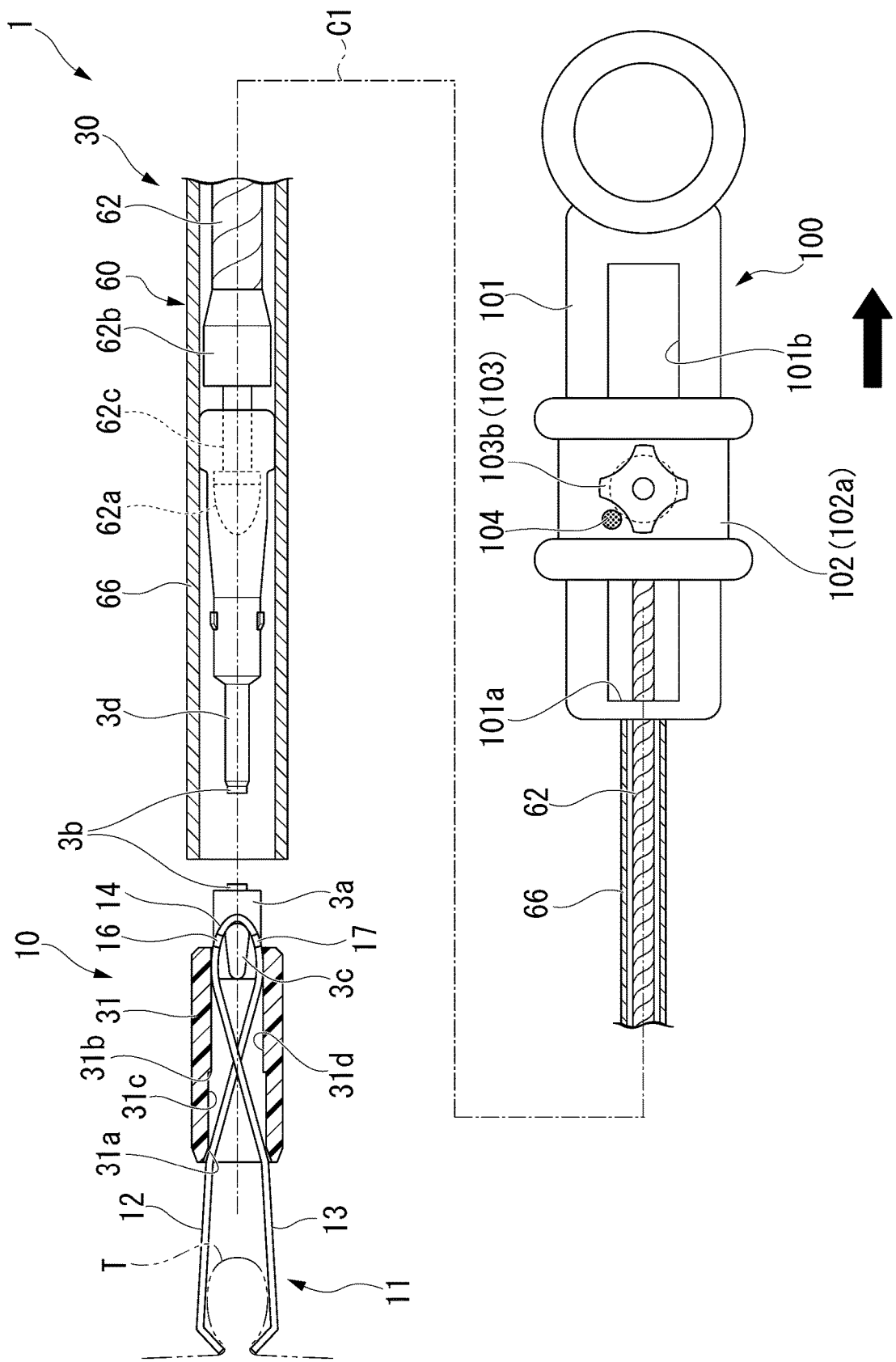

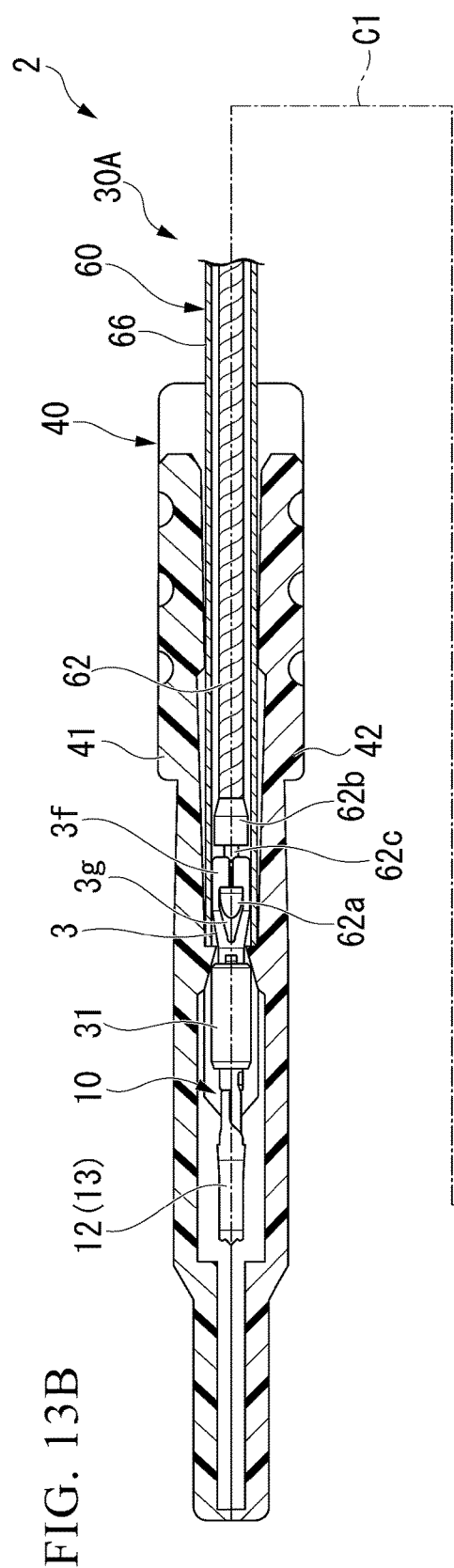
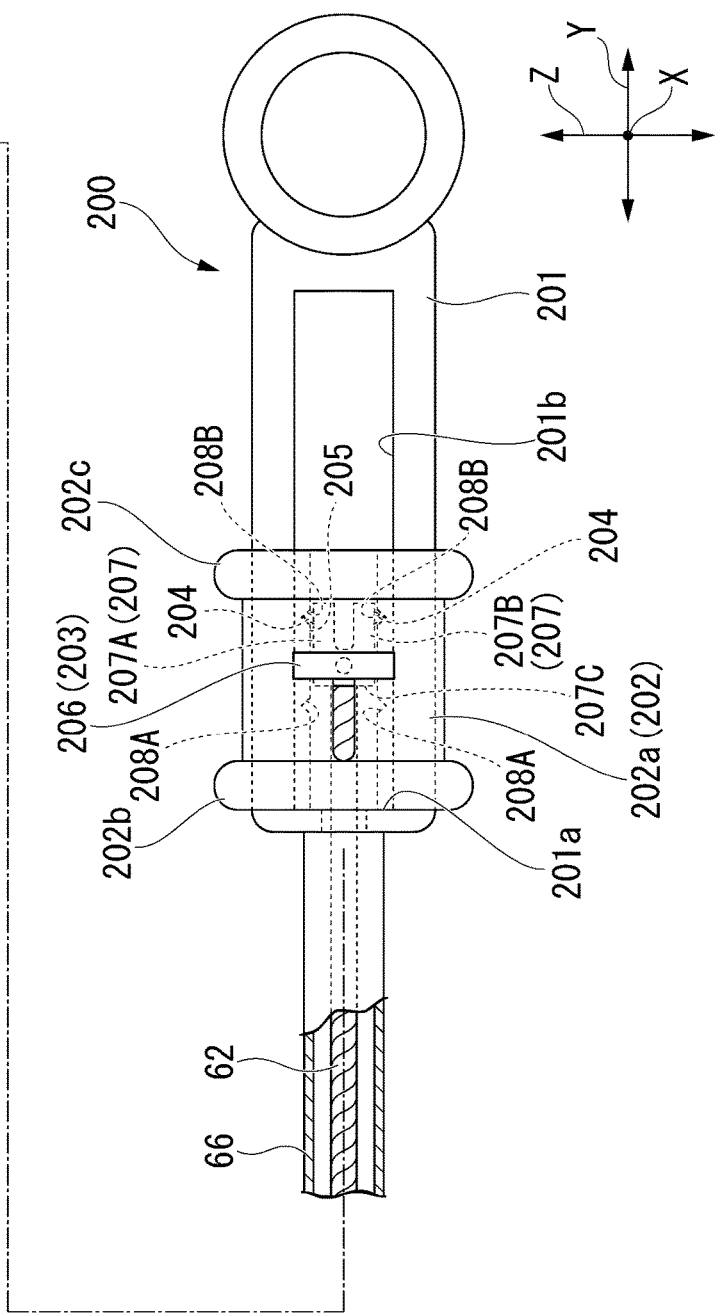
FIG. 13B

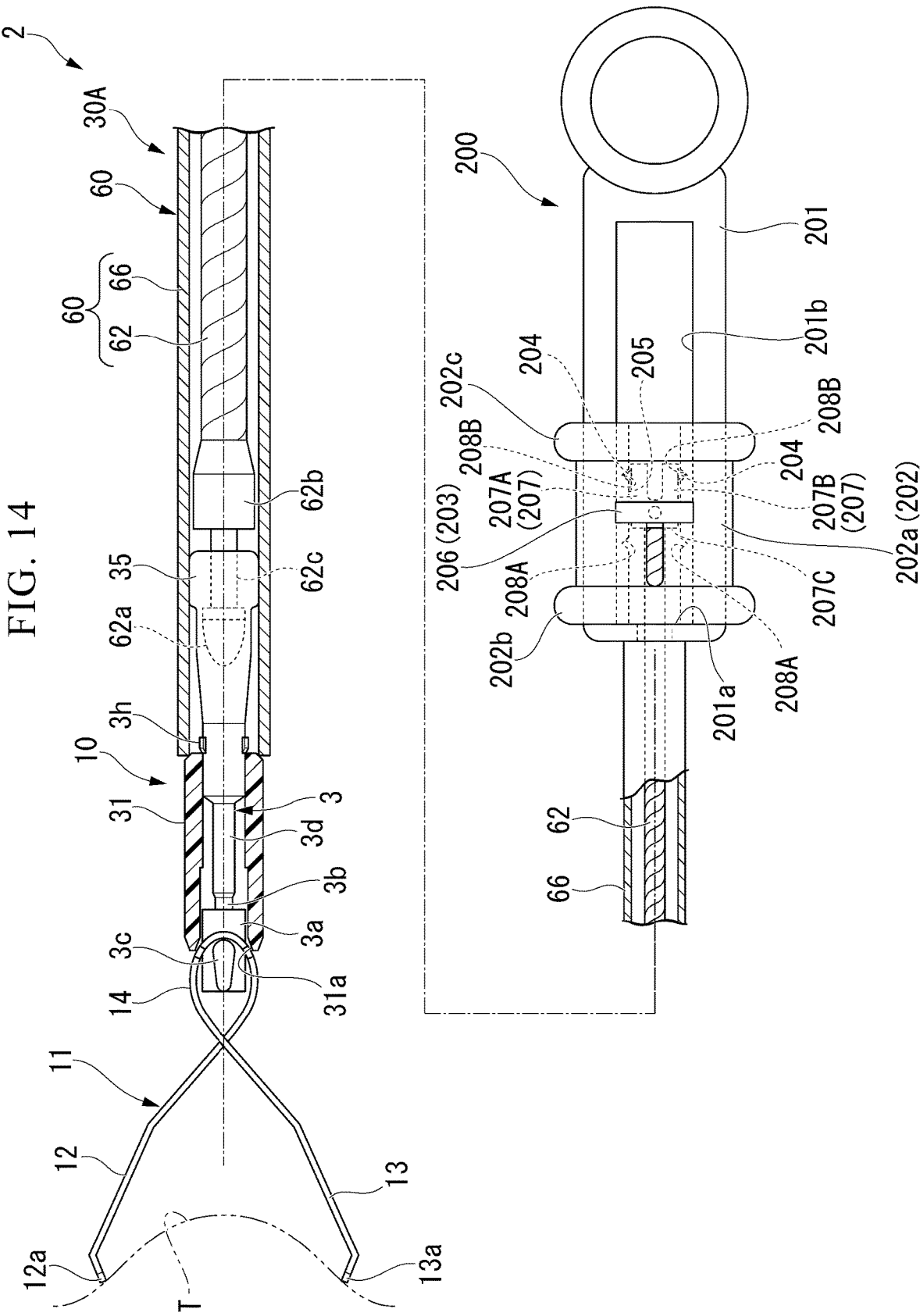

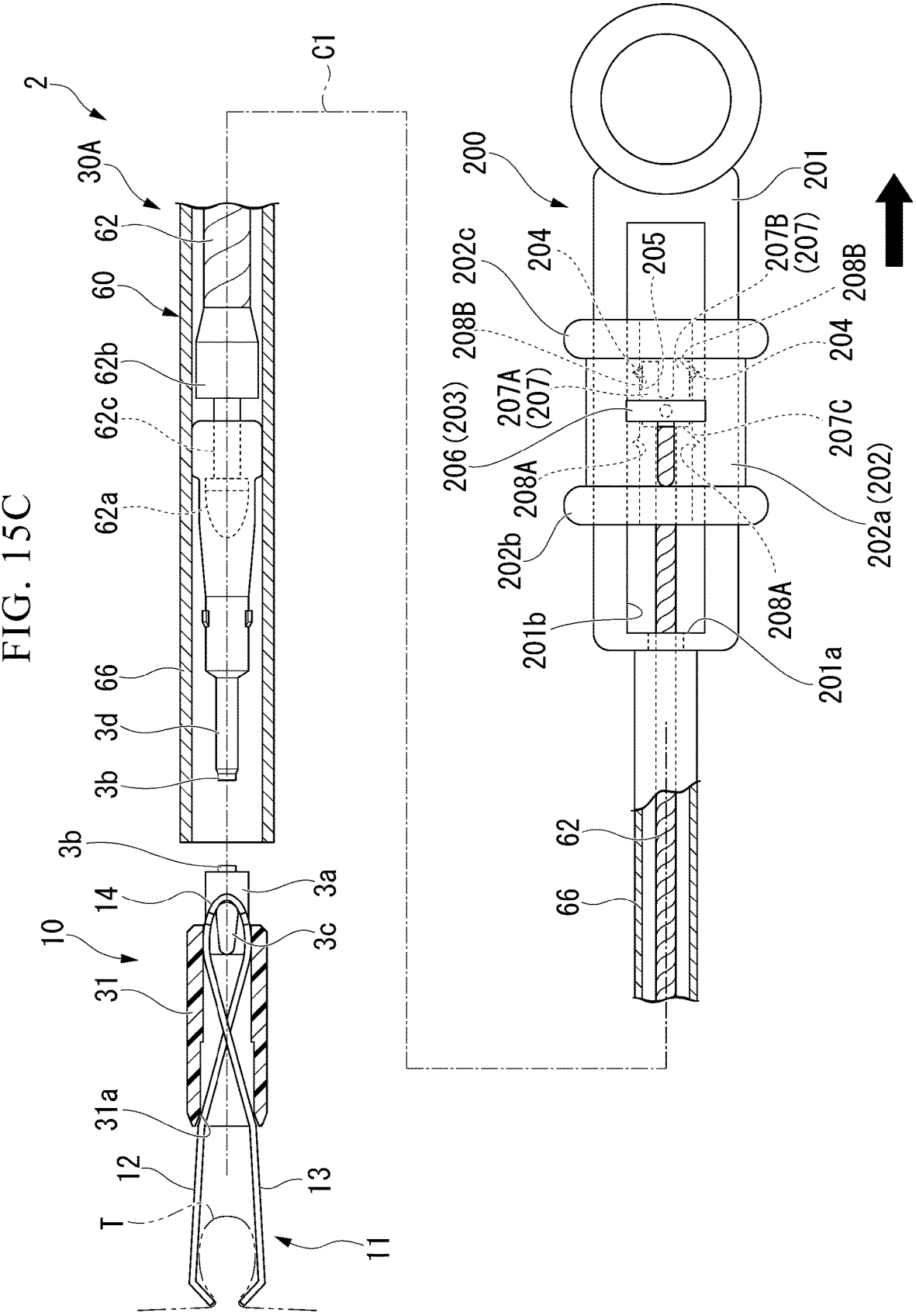

APPLICATOR, MEDICAL APPARATUS, AND OPERATION METHOD OF MEDICAL APPARATUS

CROSS REFERENCE TO RELATED APPLICATIONS

The present application is a continuation application based on a PCT Patent Application No. PCT/JP2018/046121, filed on Dec. 14, 2018, the entire content of which is hereby incorporated by reference.

BACKGROUND

Technical Field

The present disclosure relates to an applicator for treating a target tissue in a body, a medical apparatus (more specifically, a ligation apparatus used to ligate tissue), and an operation method of the medical apparatus.

Background

Conventionally, known endoscopic treatment tools are introduced into a patient's body via an endoscopic channel in order to ligate an opening or a blood vessel formed in a target tissue in a body.

Generally, a medical apparatus for treating (ligating) a target tissue in the body is configured by connecting a treatment tool (for example, a clip) inserted in the body with an applicator for adjusting the position and orientation of the treatment part at the operator's hand. When treating a target tissue in the body using such a medical apparatus, for example, additional treatment may be performed on a new target tissue that could not be found by a preoperative examination. As an example, when a clip is used as a treatment tool, for example, it is necessary to replace the plurality of clips in order to ligate each of the plurality of target tissues. In other words, in a medical apparatus for treating a target tissue in the body, it is preferable to be able to reload the so-called treatment tool by loading a new treatment tool to the applicator.

On the other hand, when treating one target tissue in the body, it may be necessary to temporarily release the state of grasping the tissue by the treatment tool and then grasp the target tissue again, that is, a so-called re-grasping operation of the treatment tool, for example, when a clip used as a treatment tool is used to accidentally grasp an unintended tissue, or when it is desired to adjust the state of grasping the target tissue.

Therefore, in order to appropriately treat the target tissue in the body, it is preferable that the medical apparatus can reload the treatment portion and the treatment tool can re-grasp the target tissue.

However, a known endoscopic treatment tool does not permit both reloadability of the treatment tool and re-grasping of the target tissue by the treatment tool. Instead, in the known treatment tool, when the slider is moved to a clip release position, which is the position where the slider is most pulled out from the base part, the connecting hook is opened to release the clip. In other words, when the slider is moved to the position closest to the distal end with respect to the base part, the connecting hook protrudes from the distal end of the inner sheath, so as to be opened by its own elastic force. Therefore, in the known endoscopic treatment tool, different clips can be loaded to the connecting hooks at the clip release position, and so-called clips can be reloaded.

On the other hand, when treating the target tissue in the body, in order to adjust the grasping state of the target tissue by the clip, the slider is moved from a clip connection position to the distal end side with respect to the base part. However, such movement may move the endoscopic treatment tool to the clip open position and release the connection state between the clip and the connection hook. That is, the known endoscopic treatment tool does not consider a re-grasping operation of the target tissue by the treatment tool, and it is not possible to achieve both reloadability of the treatment tool and re-grasping of the target tissue by the known treatment tool.

SUMMARY

The present disclosure provides an applicator and a medical apparatus (for example, a ligation apparatus) that realizes both reloadability of a treatment tool and a re-grasping operation of a target tissue by the treatment tool. Also, the present disclosure provides a method of operating the medical apparatus.

In particular, disclosed herein is an applicator capable of operating a clip unit including a first link. The applicator includes: a second link capable of engaging with the first link; an operation wire that can advance and retract the second link; a sheath capable of accommodating the second link so that engagement between the first link and the second link cannot be disengaged; a slider that is connected to the operation wire and can be operated to advance and retract the second link; and a knob that can be operated to adjust a length of the operation wire extending from the slider to the second link. In a state where the slider is in an advanced-most position at which the slider cannot be operated to further advance the second link, the knob can be operated to adjust the length of the operation wire extending from the slider to the second link between: a first length at which the second link protrudes from the sheath, and a second length that is shorter than the first length, and at which the second link is positioned in the sheath.

The applicator may further include a restricting portion that restricts a change of a distance from the first operating part to the second link by an operation of the second operating part.

The second operating part may include a rotating member around which at least a part of the operation wire is wound. The operation wire may be wound around the rotating member by a rotational movement of the rotating member.

The applicator may further include a restricting portion that restricts a change of a distance from the first operating part to the second link by restricting the rotational movement of the rotating member.

The second operating part may include a slide member that is movably engaged with the first operating part. The operation wire may be fixed to the slide member of the second operating part.

The slide member may have a protrusion that locks to the first operating part. The protrusion may be provided at a position where it is locked to the first operating part in a state where a distance from the first operating part to the second link is changed to the second length by moving the slide member with respect to the first operating part.

The second operating part may be provided in the first operating part.

The present disclose also relates to a medical apparatus that includes: a clip unit having a first arm, a second arm, and a first link; and the applicator capable of operating the clip unit.

The clip unit may be formed in a tubular shape and includes a holding tube into which the first arm and the second arm can be inserted. The first link may be connected to the first arm and the second arm, and is arranged at a position protruding from the holding tube.

In a state where a distance from the first operating part to the second link is the second length, when the first operating part is in a most advanced position, the holding tube and the sheath may be in contact with each other.

The applicator may further include a restricting portion that restricts a change of a distance from the first operating part to the second link by an operation of the second operating part.

The second operating part may include a rotating member around which at least a part of the operation wire is wound. The operation wire may be wound around the rotating member by a rotational movement of the rotating member.

The applicator may further include a restricting portion that restricts a change of a distance from the first operating part to the second link by restricting the rotational movement of the rotating member.

The second operating part may include a slide member that is movably engaged with the first operating part. The operation wire may be fixed to the slide member of the second operating part.

The slide member may have a protrusion that locks to the first operating part. The protrusion may be provided at a position where it is locked to the first operating part in a state where a distance from the first operating part to the second link is changed to the second length by moving the slide member with respect to the first operating part.

The second operating part may be provided in the first operating part.

The present disclosure also relates to a method for operating a medical apparatus. The method includes: advancing a second link of an applicator to advanced-most position by operating a slider of the applicator; adjusting a length of an operation wire extending from the slider to the second link to a first length by operating a knob that can adjust the length of the operation wire extending from the slider to the second link between the first length and a second length shorter than the first length; and engaging and/or disengaging a first link of the clip unit and the second link of the applicator in a state where the slider is in the advanced-most position and the length of the operation wire extending from the slider to the second link is the first length.

The operation method may further include: performing engagement operation between the first link and the second link, by advancing the first operating part most and adjusting the length of the operation wire from the first operating part to the second link to the first length; and adjusting the length of the operation wire from the first operating part to the second link from the first length to the second length, after performing the engagement operation.

The operation method may further include: adjusting the length of the operation wire from the first operating part to the second link to the first length or the second length, by winding or unwinding the operation wire wound around a rotating member provided in the second operating part.

The operation method may further include: adjusting the length of the operation wire from the first operating part to the second link to the first length or the second length, by advancing and retreating a slide member provided in the second operating part with respect to the first operating part.

According to each of the above-described aspects of the medical apparatus and the applicator, it is possible to realize both reloadability of the treatment tool and a re-grasping operation of the target tissue by the treatment tool. Further, according to each of the above aspects of the operation method of the medical apparatus, the clip unit can be suitably loaded to the medical apparatus by engaging the clip unit with the applicator.

BRIEF DESCRIPTION OF THE DRAWINGS

FIG. 6A is a diagram showing an operation of loading a clip unit to a treatment tool main body.

FIG. 6B is a diagram showing an operation of loading a clip unit to a treatment tool main body.

FIG. 6C is a diagram showing an operation of loading a clip unit to a treatment tool main body.

FIG. 6E is a diagram showing an operation of loading a clip unit to a treatment tool main body.

FIG. 11A shows an operation of treating a target tissue using the medical apparatus.

FIG. 11B is a diagram showing an operation of treating a target tissue using the medical apparatus.

FIG. 13B is a diagram showing an operation of treating a target tissue using the medical apparatus.

FIG. 14 is a diagram showing an operation of treating a target tissue using the medical apparatus.

FIG. 15C is a diagram showing an operation of treating a target tissue using the medical apparatus.

DETAILED DESCRIPTION

Hereinafter, the configuration of a medical apparatus according to an exemplary embodiment of the present disclosure will be described with reference to FIGS. 1 to 11.

A medical apparatus 1 according to the present embodiment is used by being inserted into the patient's body through a channel formed in an endoscope (not shown). More specifically, the medical apparatus 1 according to the present embodiment is a ligation apparatus for ligating a target tissue in the body.

In the present specification, the side where the endoscope operating part for the operator to operate the endoscope is positioned is defined as the proximal end side, and the side where the distal end portion of the endoscope inserted into the body is positioned is defined as the distal end side.

Figure 8:
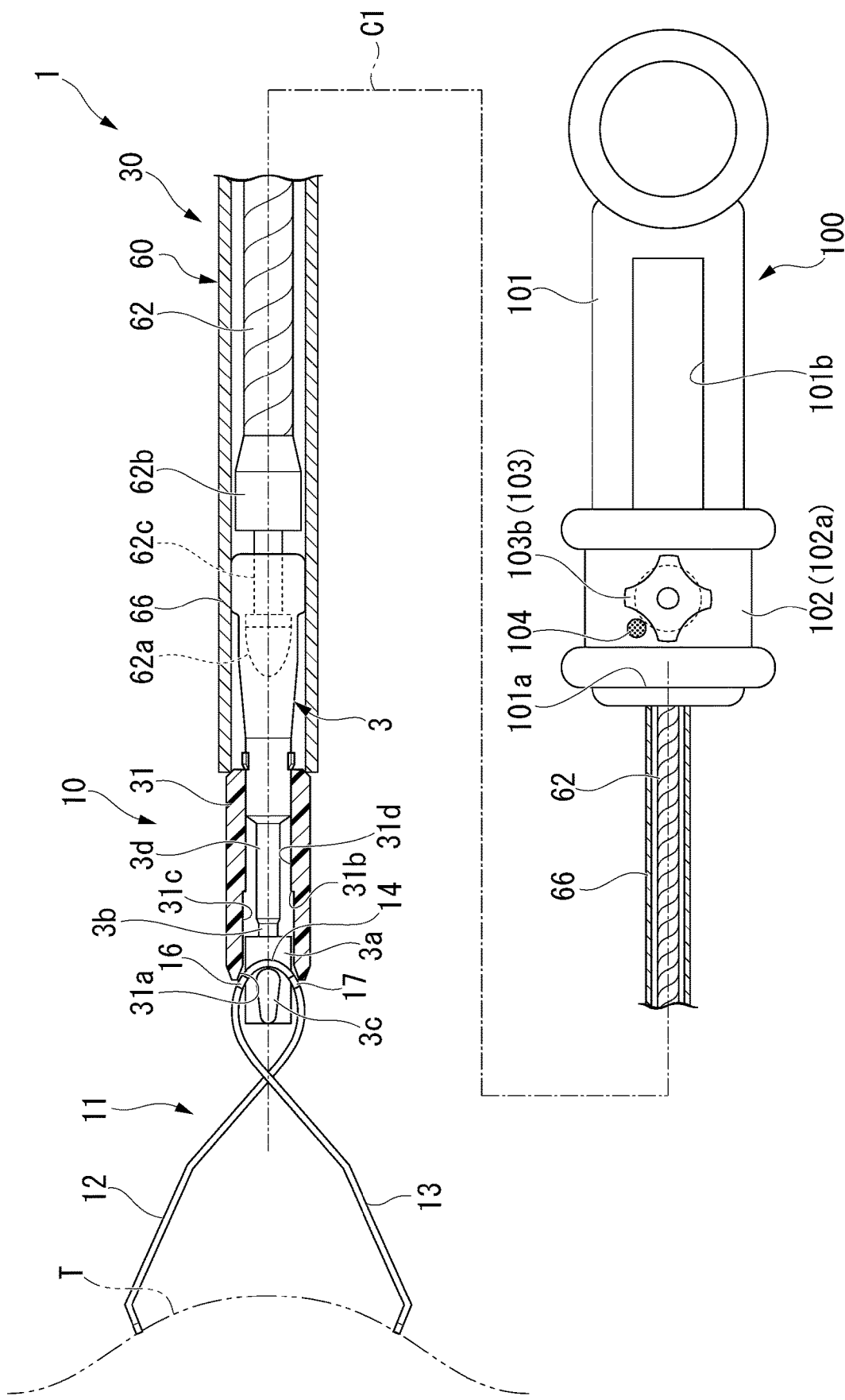
FIG. 8 is a diagram showing an operation of treating a target tissue using the medical apparatus.

The medical apparatus 1 according to the present embodiment is configured by including a clip unit (treatment tool) 10 provided on the distal end side and a treatment tool main body (applicator) 30 (see FIG. 8). Hereinafter, for convenience of explanation, the clip unit 10 will be abbreviated as a clip 10. As shown in FIG. 8, the clip 10 is removably connected to the distal end portion of the treatment tool main body 30, which will be described later.

(Configuration of Clip 10)

Figure 1:
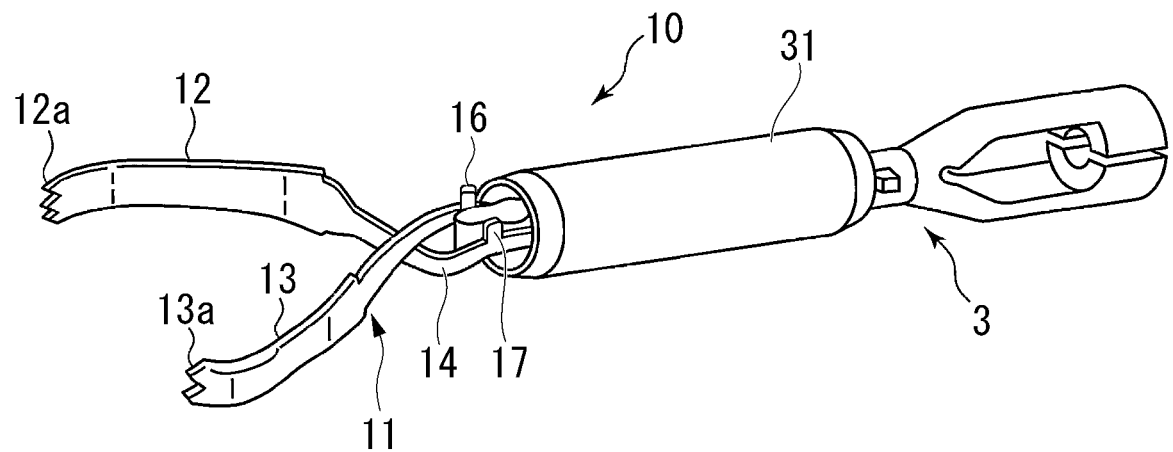
FIG. 1 is a perspective view schematically showing a configuration of a clip unit according to an exemplary embodiment of the present disclosure.
Figure 2:
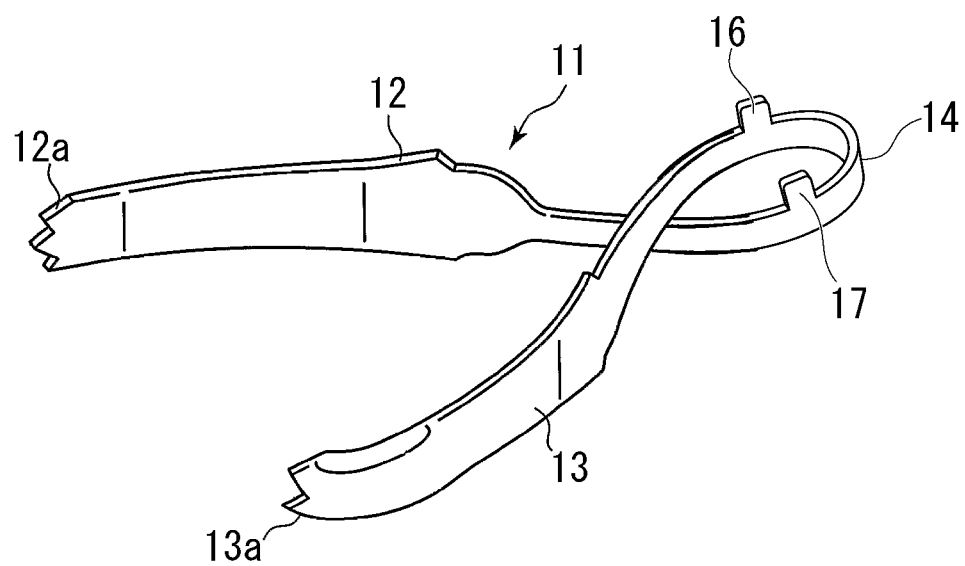
FIG. 2 is a perspective view schematically showing a configuration of an arm member in the clip unit.
Figure 3A:
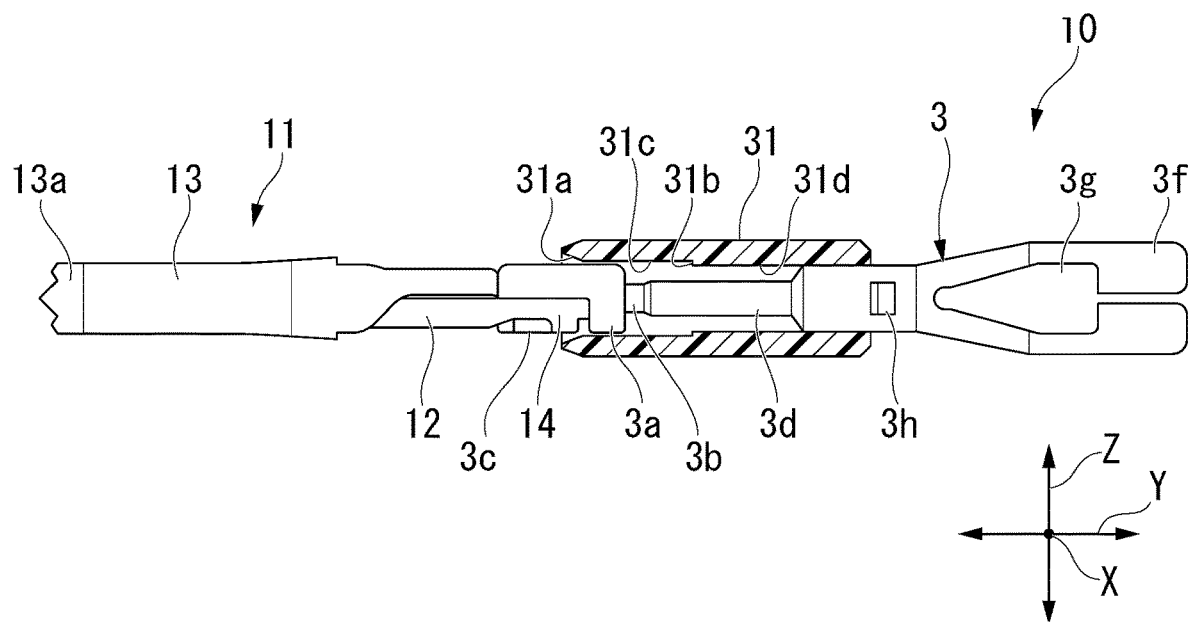
FIG. 3A is a partial cross-sectional view of the clip unit in side view.
Figure 3B:
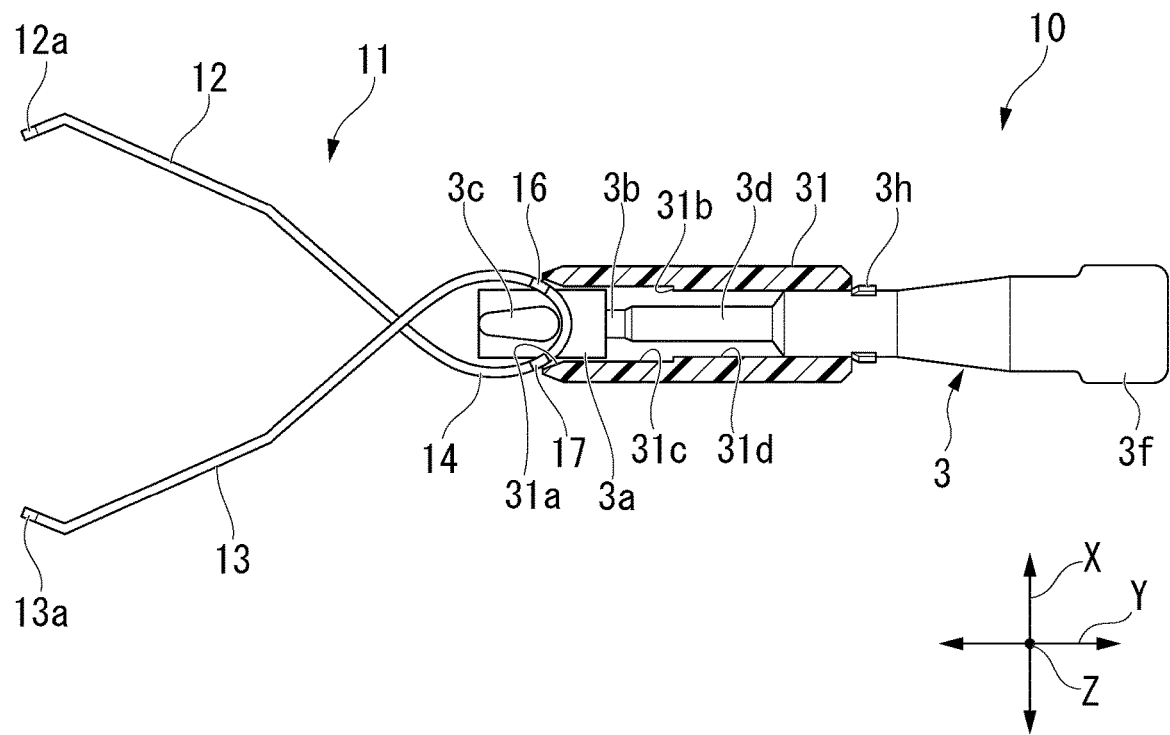
FIG. 3B is a partial cross-sectional view of the clip unit in plan view.

FIG. 1 is a perspective view of the clip 10 according to the present embodiment. FIG. 2 is a perspective view of the arm member 11 of the clip 10 according to the present embodiment. FIG. 3A is a partial cross-sectional view of the arm member 11 in plan view. FIG. 3B is a partial cross-sectional view of the arm member 11 in side view.

As shown in FIG. 1, the clip 10 according to the present embodiment includes an arm member 11, a holding tube 31, and a connecting member (first link) 3.

In the present specification, as shown in FIG. 3B, an opposite direction X where the first arm 12 and the second arm 13 of the arm member 11 of the clip 10 face each other, an axial direction Y parallel to the axis C1 of the holding tube 31, and an orthogonal direction Z orthogonal to each of the opposite direction X and the axial direction Y are defined. Further, for convenience of explanation, the axis C1 of the insertion portion 60, which will be described later, is regarded as the axis of the clip 10.

The arm member 11 has a first arm 12, a second arm 13, and an intermediate portion 14. The first arm 12 and the second arm 13 extend from the proximal end side toward the distal end side and are arranged so as to face each other. The intermediate portion 14 is positioned between the proximal end of the first arm 12 and the proximal end of the second arm 13. In the present embodiment, as shown in FIG. 1, the first arm 12 and the second arm 13 may be formed at positions line-symmetrical with respect to the axis C1.

In the present embodiment, the first arm 12 and the second arm 13 have an elastic restoring force such that, in a natural state, they are separated from each other and the distance between them increases along the direction from the proximal end side to the distal end side. In the present specification, the term "natural state" means a state in which an external force does not act on the arm member 11. A claw 12a extending toward the second arm 13 side is formed at the distal end of the first arm 12. A claw 13a extending toward the first arm 12 side is formed at the distal end of the second arm 13.

In the present embodiment, the arm member 11 is formed by, for example, forming the first arm 12 and the second arm 13 by bending a metal material such as a leaf spring material such as stainless steel, and then crossing the first arm 12 and the second arm 13. With this structure, the arm member 11 can slide along the inner peripheral surface of the holding tube 31 when it is pulled into the holding tube 31.

A pair of protrusions 16 and 17 are formed in the intermediate portion 14 of the arm member 11. More specifically, the pair of protrusions 16 and 17 protrude at right angles to the longitudinal direction in which the first arm 12 and the second arm 13 of the arm member 11 extend. The pair of protrusions 16 and 17 may be formed at positions line-symmetrical with respect to the axis C1. By forming the pair of protrusions 16 and 17 of the clip 10, when the arm member 11 is pulled into the holding tube 31, as described later, the pair of protrusions 16 and 17 bite into the inner wall on the proximal end side of the stepped portion 31b of the holding tube 31, so that the movement (advance) of the arm member 11 with respect to the holding tube 31 can be restricted.

In the present embodiment, the holding tube 31 is formed in a cylindrical shape and has an inner diameter through which the proximal end portion of the arm member 11 can enter. That is, the holding tube 31 is formed with lumens through which the first arm 12 and the second arm 13 of the arm member 11 can enter. Further, at least a part of the connecting member 3 described later can enter the lumen formed in the holding tube 31. In the present embodiment, a stepped portion 31b is formed so as to protrude inward in the radial direction of the holding tube 31 from the inner wall of the holding tube 31. The holding tube 31 is formed to have a large diameter portion 31c positioned on the distal end side of the stepped portion 31b and a small diameter portion 31d positioned on the proximal end side of the stepped portion 31b. That is, in the holding tube 31, the large diameter portion 31c has a larger inner diameter than the small diameter portion 31d. In the present embodiment, the large-diameter portion 31c of the holding tube 31 has an inner diameter that allows the pair of protrusions 16 and 17 of the arm member 11 to freely advance and retract. Further, the small diameter portion 31d of the holding tube 31 has an inner diameter smaller than the width of the portion where the pair of protrusions 16 and 17 are formed in the arm member 11. Therefore, as will be described later, when the arm member 11 is pulled into the holding tube 31 and is positioned closer to the proximal end side than the stepped portion 31b, the pair of protrusions 16 and 17 of the arm member 11 bite into the inner wall of the small diameter portion 31d of the holding tube 31, so that the movement of the arm member 11 toward the distal end side with respect to the holding tube 31 is restricted.

Further, in the present embodiment, the pressing tube 31 is formed so that the outer diameter is larger than the inner diameter of the sheath 66 of the insertion portion 60, which will be described later.

These members constituting the clip 10, including the arm member 11, are formed of a material such as a cobalt-chromium alloy, titanium, or stainless steel. The clip 10 is configured so that it can be observed under MRI (magnetic resonance imaging) fluoroscopy.

The arm member 11 is formed integrally by punching, for example, a plate material made of a cobalt-chromium alloy or the like into a shape in which the first arm 12, the second arm 13, the intermediate portion 14, and the pair of protrusions 16 and 17 are developed in a plane shape.

The first arm 12 and the second arm 13 of the arm member 11 have an elastic restoring force that moves in the direction in which the distal ends thereof are separated from each other, that is, in the direction in which the arm member 11 opens.

As shown in FIGS. 3A and 3B, a tapered surface 31a is formed on the inner wall of the distal end of the holding tube 31 over the entire circumference. The diameter of the tapered surface 31a increases toward the distal end side. In the present embodiment, the holding tube 31 and the locking portion 32 may be integrally formed of a material such as a 64 titanium alloy (Ti-6AL-4V) or a cobalt-chromium alloy.

(Configuration of Connecting Member 3)

In the present embodiment, as shown in FIGS. 3A and 3B, the connecting member (first link) 3 is formed by including a distal end portion 3a, a small diameter portion 3b, a hook portion 3c, a medium diameter portion 3d, a large diameter portion 3e, a notch portion 3g, a proximal end portion 3f, and a protrusion portion 3h. The connecting member 3 is formed by a method such as injection molding using a resin material having a predetermined strength.

In the present embodiment, the connecting member 3 is configured to connect the arm member 11 of the clip 10 and the operation wire 62 described later. The distal end portion 3a of the connecting member 3 is configured to support the hook portion 3c for connecting the arm member 11, and the shape thereof is not particularly limited. The hook portion 3c is formed so as to protrude from the distal end portion 3a in a direction orthogonal to the longitudinal direction in which the connecting member 3 extends, and by hooking the hook portion 3c on a loop formed in the intermediate portion 14 of the arm member 11, the arm member 11 can be connected to the connecting member 3. The small diameter portion 3b is formed by being connected to the proximal end side of the distal end portion 3a. The small diameter portion 3b is a portion of the connecting member 3 having the smallest outer diameter, and the small diameter portion 3b breaks when an operating force amount equal to or greater than a predetermined value is applied. In the present embodiment, for example, when a tensile force of 20 to 60 Newton is applied to the small diameter portion 3b, the small diameter portion 3b breaks. The medium-diameter portion 3d and the large-diameter portion 3e are formed to have a larger outer diameter than the small-diameter portion 3b, and are portions that connect the distal end portion 3a and the proximal end portion 3f of the connecting member 3. In the present embodiment, since the outer diameters of the medium diameter portion 3d and the large diameter portion 3e are equal to or smaller than the inner diameter of the holding tube 31, the connecting member 3 can enter the holding tube 31 when the connecting member 3 moves with respect to the holding tube 31.

In the present embodiment, as shown in FIG. 3A, the proximal end portion 3f of the connecting member 3 is formed by being bifurcated from the distal end side to the proximal end side. More specifically, the proximal end portion 3f is formed by a pair of separated arms. As shown in FIG. 1, a hole is formed having a size such that an arrowhead-shaped hook 62a (see FIG. 4A) formed at the distal end of the operation wire 62, which will be described later, can enter between the pair of arms at the proximal end portion 3f. For example, when the hook 62a is inserted into the hole formed in the proximal end portion 3f, the outer peripheral surface of the hook 62a presses while abutting against the inner peripheral surface of the above-mentioned hole, whereby a pair of arms of the proximal end portion 3f are elastically deformed outward in the longitudinal axis direction of the connecting member 3. Therefore, the hook 62a can pass through the hole formed in the proximal end portion 3f and enter the notch portion 3g described later.

As shown in FIG. 3A, a notch portion 3g is formed by cutting off a part of the proximal end portion 3f. The notch portion 3g has a size capable of receiving the hook 62a in a state where the hook 62a, which will be described later, can enter through the hole formed in the proximal end portion 3f.

A protrusion portion 3h is formed on the outer peripheral surface of the large diameter portion 3e of the connecting member 3. The connecting member 3 can engage with the holding tube 31 at the position where the protrusion portion 3h is formed. By configuring the connecting member 3 in this way, it is possible to restrict the movement of the connecting member 3 with respect to the holding tube 31 by the elastic restoring force of the arm member 11.

(Configuration of Treatment Tool Main Body 30)

Subsequently, the configuration of the treatment tool main body (applicator) 30 according to the present embodiment will be described.

Figure 4A:
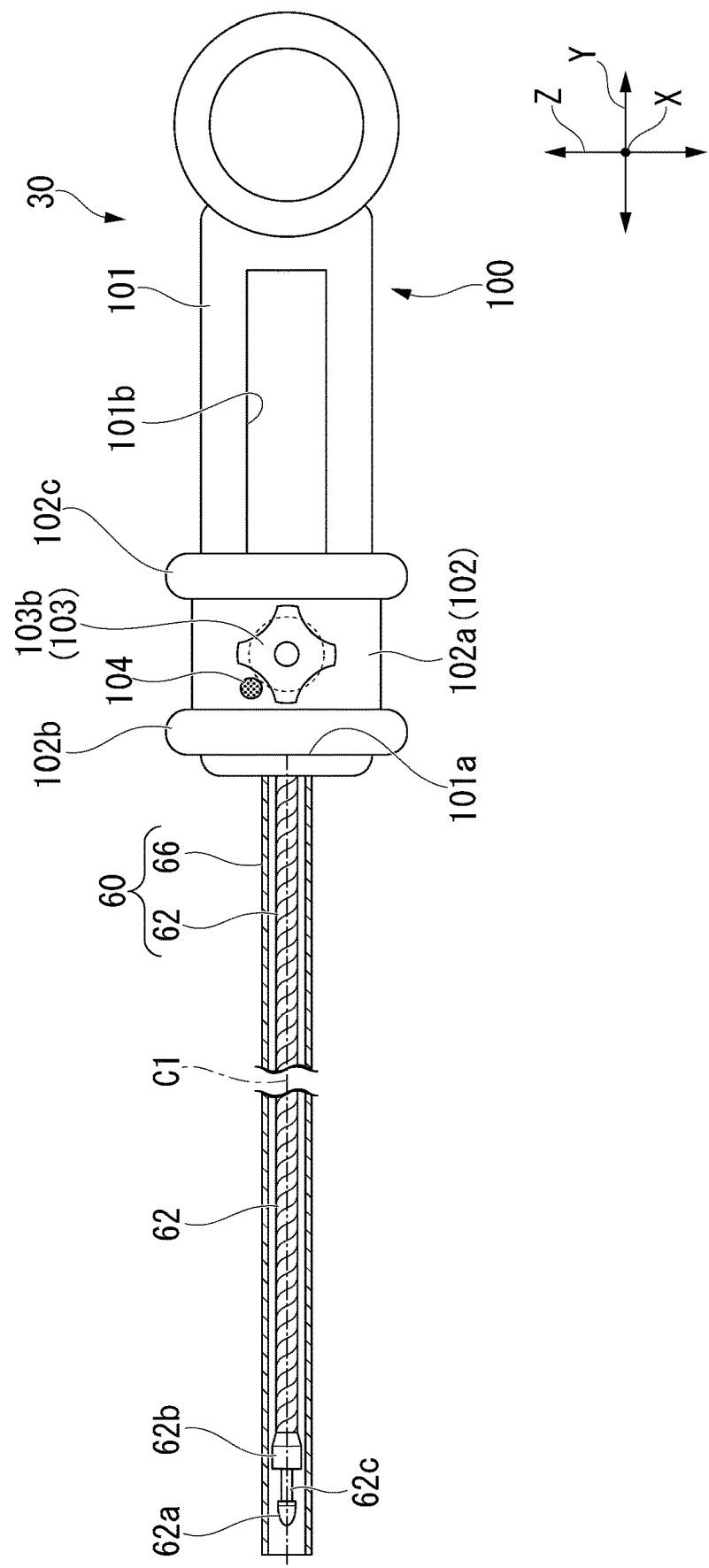
FIG. 4A is a partial cross-sectional view of the treatment tool main body in plan view.
Figure 4B:
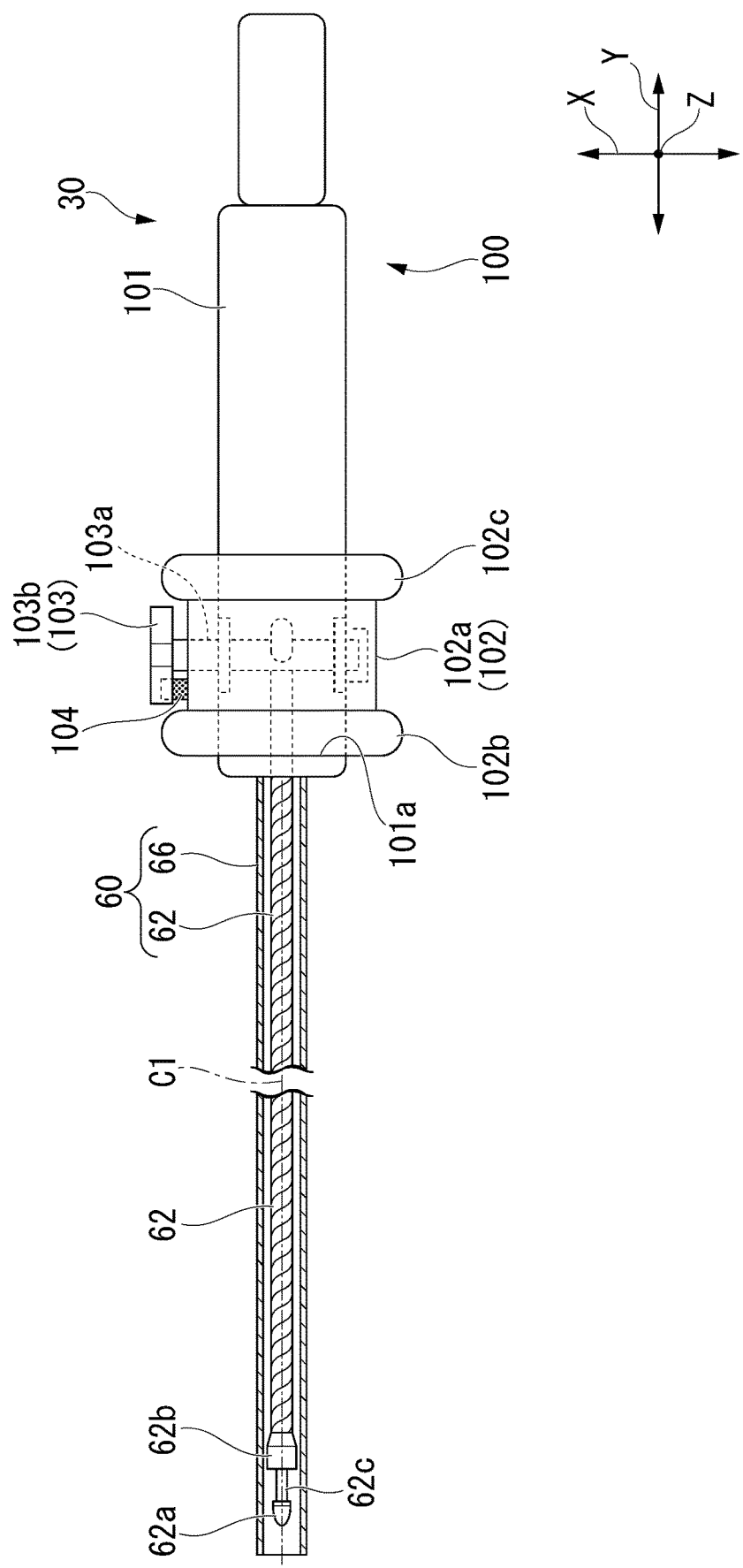
FIG. 4B is a partial cross-sectional view of the treatment tool main body in side view.

As shown in FIGS. 4A and 4B, the treatment tool main body 30 according to the present embodiment includes an insertion portion 60 and an operating part 100.

The insertion portion 60 is positioned on the distal end side of the operating part 100 and is connected to the distal end of the operating part 100. On the other hand, the operating part 100 is attached to the proximal end portion of the insertion portion 60.

(Configuration of Insertion Portion 60)

The insertion portion 60 of the treatment tool main body 30 includes a sheath 66 and an operation wire (wire) 62. The operation wire 62 is inserted into the sheath 66 so as to be able to advance and retract. The operation wire 62 is provided for the operator to transmit the force for operating the operating part 100 on the proximal end side (for example, the operation of pushing the slider 102 and the operation of pulling back the slider 102) to the clip 10.

The sheath 66 may be a coil sheath made of stainless steel such as SUS301 having high compression strength, for example. In this case, as the sheath 66, a coil formed by tightly winding a wire (not shown) in the axial direction Y can be used. The sheath 66 has flexibility and is strong against a compressive force in the axial direction Y.

Figure 7A:
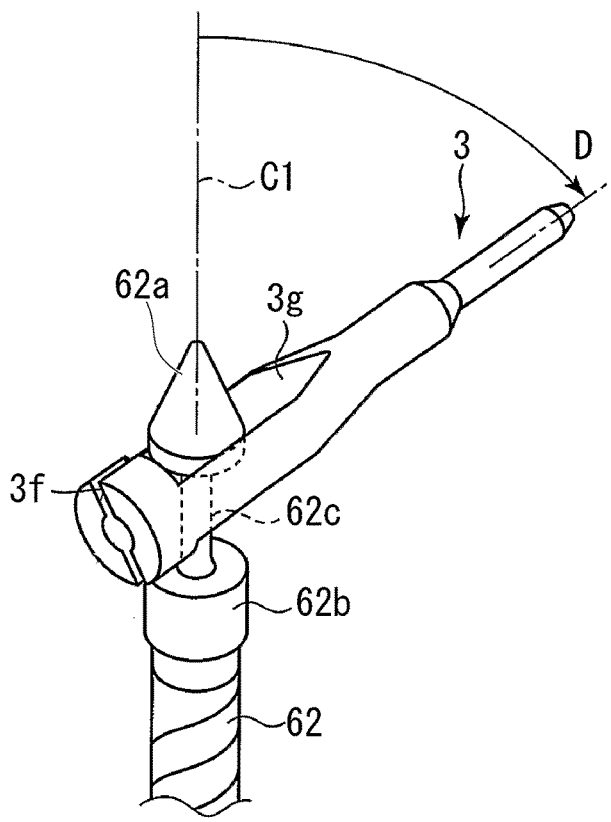
FIG. 7A is a perspective view showing a connecting structure of a treatment tool main body and a clip unit.
Figure 7B:
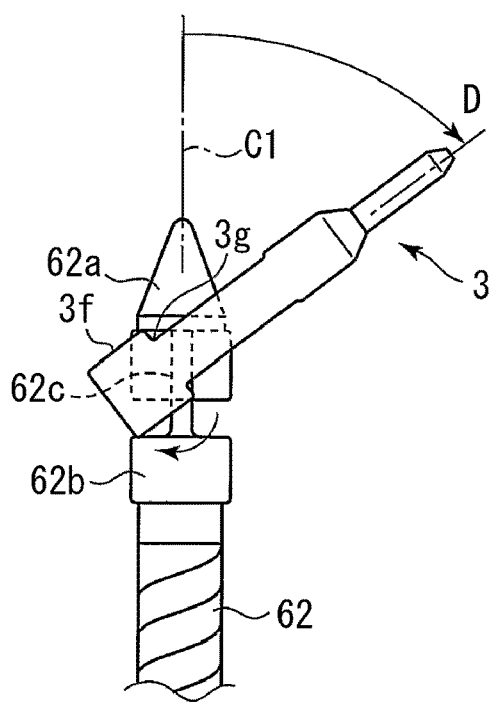
FIG. 7B is a plan view showing a connection structure between a treatment tool main body and a clip unit.

In the present embodiment, the sheath 66 is formed with an inner diameter such that the connecting member 3 cannot rotate with respect to the hook 62a when the sheath 66 is positioned in the sheath 66 in a state where the hook 62a and the notch 3g of the connecting member 3 are engaged with each other. More specifically, as shown in FIGS. 7A and 7B, in the above-mentioned state, it is sufficient that the connecting member 3 rotates in a direction intersecting the hook 62a in the axis C1 direction and the engagement state between the hook 62a and the connecting member 3 is not released, and it does not mean that the connecting member 3 does not rotate with respect to the hook 62a at all.

In the present embodiment, the operation wire 62 is formed of, for example, a single metal wire or a stranded wire. The operation wire 62 is configured by connecting a hook (second link) 62a, a shaft portion 62c, and a fixing portion 62b on the distal end side. The fixing portion 62b is a cylindrical member made of a metal material such as stainless steel, for example. The operation wire 62 is fixed to the fixing portion 62b by various known methods such as adhesion and welding. Further, the hook 62a and the fixing portion 62b are connected by a shaft portion 62c formed in a rod shape. Therefore, in the present embodiment, the operation wire 62, the hook 62a, the fixing portion 62b, and the shaft portion 62c are integrally formed. The hook 62a can move forward and backward together with the operation wire 62 by moving the operation wire 62 forward and backward.

The hook 62a is formed in a conical shape. As shown in FIGS. 7A and 7B, the hook 62a has an outer peripheral surface having a slope shape in which the outer diameter gradually decreases toward the distal end side. The outer diameter of the hook 62a on the proximal end surface is larger than the diameter of the hole formed in the proximal end portion 3f in a state where the proximal end portion 3f of the connecting member 3 is not elastically deformed.

That is, in a state where the hook 62a is housed in the notch 3g of the connecting member 3, the hook 62a does not come off from the notch 3g only by the advancing/retracting operation of the operation wire 62.

(Configuration of Operating Part 100)

As shown in FIGS. 4A and 4B, the operating part 100 includes an operating part main body (handle) 101, a slider (first operating part) 102, and a wire adjusting member (second operating part) 103.

The operating part main body 101 is attached to the proximal end portion of the sheath 66. The operating part main body 101 is formed in a rod shape extending in the axial direction Y, and a finger hook portion is provided at the proximal end portion. A slit 101b extending in the axial direction Y is formed in the operating part main body 101.

The slider 102 is provided so as to be inserted through the operating part main body 101. The slider 102 can slide (forward and backward) in the axial direction Y with respect to the operating part main body 101. In the present embodiment, when the slider 102 is moved forward or backward in the axial direction Y, the operation wire 62 and the hook 62a fixed to the distal end of the operation wire 62 are moved forward or backward. Further, in a state where the operation wire 62 and the connecting member 3 are connected, the arm member 11 of the clip 10 can move forward or backward together with the operation wire 62 by the forward or backward operation of the operation wire 62. As a result, the pair of first arm 12 and second arm 13 of the arm member 11 can be opened or closed.

The slider 102 is formed in a cylindrical shape. A recess 102a is formed on the outer peripheral surface of the slider 102 over the entire circumference. The slider 102 is formed with a flange portion 102b, a recess 102a, and a flange portion 102c in this order from the distal end side to the proximal end side in the axial direction Y. The pair of collar portions 102b and 102c have an elliptical shape when viewed in the axial direction Y. As a result, the slider 102 can be easily grasped, and space can be saved when packing the operating part 100 of the endoscope clip 1.

By engaging the slider 102 with the slit 101b of the operating part main body 101, the movement range of the slider 102 in the axial direction Y with respect to the operating part main body 101 is limited.

As shown in FIGS. 4A and 4B, a reel-shaped wire adjusting member (second operating part) 103 and a restricting portion 104 are formed in the recess 102a of the slider 102. In the present embodiment, the wire adjusting member 103 can adjust the distance of the operation wire 62 provided between the slider 102 and the fixing portion 62b connected to the hook 62a by an operation different from the advancing/retracting operation of the slider 102 described later. In other words, the wire adjusting member 103 can adjust the distance from the slider 102 to the hook 62a.

In the present embodiment, as shown in FIGS. 4A and 4B, in a state where the slider 102 advances until it comes into contact with the distal end surface 101a of the slit 101b and a part of the operation wire 62 is wound around the shaft portion 103a, the hook 62a is positioned on the proximal end side of the opening on the distal end side of the sheath 66. That is, in this state, the hook 62a is housed in the sheath 66. Further, when the slider 102 is moved to a position where it abuts on the distal end surface 101a of the slit 101b (the most advanced position) while the operation wire 62 is not wound around the shaft portion 103a, at least the hook 62a protrudes from the opening at the distal end side of the sheath 66 (see FIGS. 6C and 6D).

As shown in FIG. 4B, the wire adjusting member (second operating part) 103 has a shaft portion 103a formed in a rod shape and a knob 103b fixed to the shaft portion 103a in order to rotate the shaft portion 103a. In the present embodiment, the shaft portion 103a may be formed by being inserted into a hole formed in the recess 102a of the slider 102 of the operating part 100, or may be formed integrally with the slider 102. That is, in the present embodiment, the wire adjusting member 103 and the slider 102 can move forward and backward integrally along the axis C1 direction. In other words, in the present embodiment, the wire adjusting member 103 and the slider 102 do not move relative to each other along the axis C1 direction.

As shown in FIG. 4B, the proximal end of the operation wire 62 is fixed to the shaft portion 103a through a through hole formed in the flange portion 102b of the slider 102.

The knob 103b of the wire adjusting member 103 can rotate the shaft portion 103a by rotating in the clockwise direction or the counterclockwise direction. In the present embodiment, by rotating the knob 103b clockwise, the shaft portion 103a also rotates clockwise, and a part of the operation wire 62 can be wound around the shaft portion 103a. Further, in the present embodiment, by rotating the knob 103b in the counterclockwise direction, the shaft portion 103a also rotates in the counterclockwise direction, and the operation wire 62 wound around the shaft portion 103a can be discharged.

In the present embodiment, the shaft portion 103a rotates together with the knob 103b, so that the length of the operation wire 62 provided between the slider 102 (more specifically, the shaft portion 103a of the wire operating member 103 fixed to the slider 102) and the fixing portion 62b connected to the hook 62a can be adjusted. In other words, the distance from the slider 102 to the hook 62a can be adjusted by rotating the shaft portion 103a together with the knob 103b.

As shown in FIGS. 4A and 4B, in the recess 102a of the slider 102, in the vicinity of the knob 103b of the wire adjusting member 103, a restricting portion 104 that restricts the rotational movement of the knob 103b is provided. In the present embodiment, the specific configuration of the restricting portion 104 is not particularly limited, but the rotational movement of the knob 103b can be restricted when the restricting portion 104 is not operated. On the other hand, the knob 103b can be rotated by pushing the restricting portion 104. More specifically, when the operator pushes the restricting portion 104 below the height of the slider 102 of the knob 103b, the knob 103 can rotate over the restricting portion 104. On the other hand, when the operator releases the pressure on the restricting portion 104, the restricting portion 104 protrudes from the surface of the slider 102 to a height similar to the height of the knob 103b and abuts on the knob 103b, so that the rotation of the knob 103b in the clockwise or counterclockwise direction can be restricted. Therefore, by providing the restricting portion 104 in the operating part 100 according to the present embodiment, it is possible to prevent the knob 103b from being erroneously operated at an unintended timing.

(Configuration of Clip Case 40)

Next, the configuration of the clip case 40 according to the present embodiment will be described with reference to FIGS. 5A to 5D. The clip case 40 is configured to be easy to transport and to prevent contamination by the external environment in the process of actually using the clip 10 according to the present embodiment after it is manufactured.

Figure 5A:
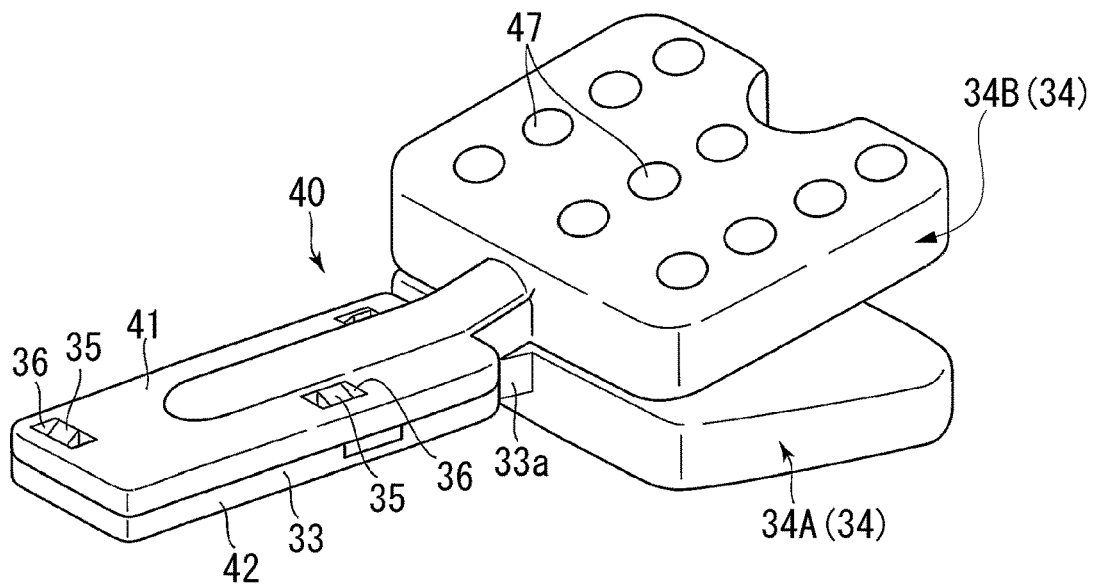
FIG. 5A is a perspective view schematically showing a configuration of a clip case.
Figure 5B:
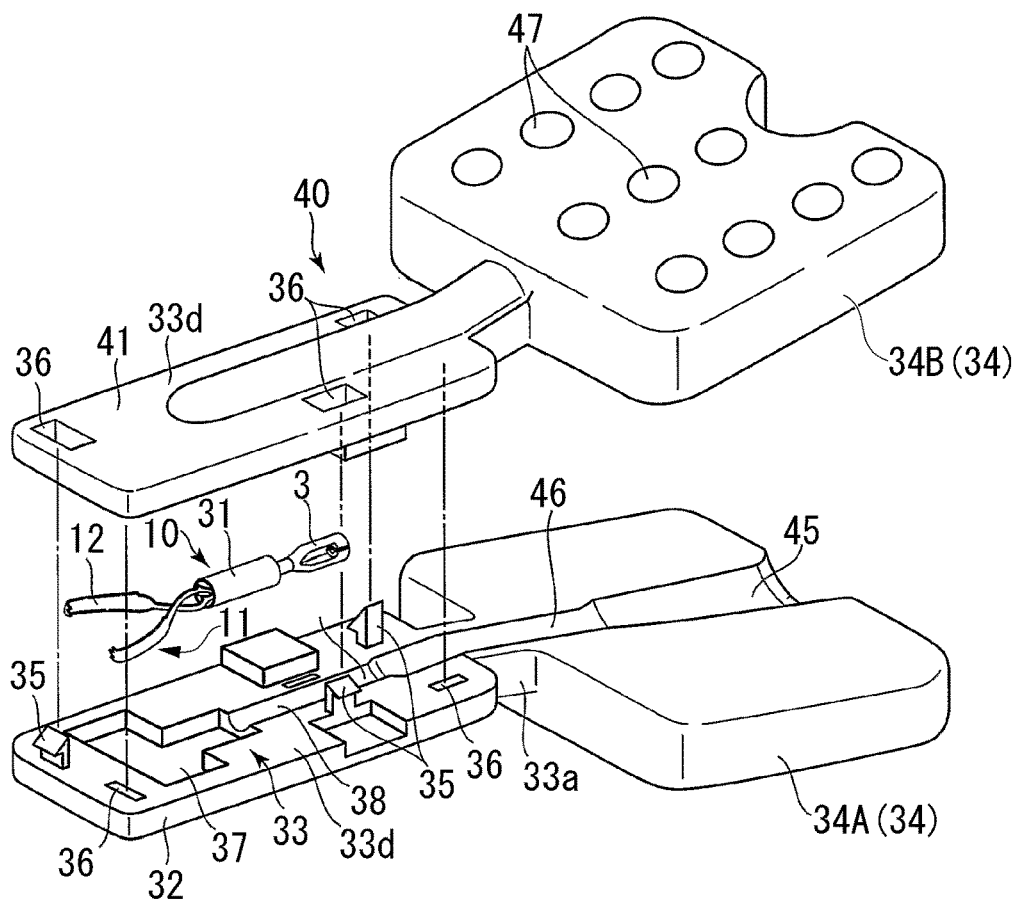
FIG. 5B is a perspective view showing a mode in which the clip unit is housed in a clip case.
Figure 5C:
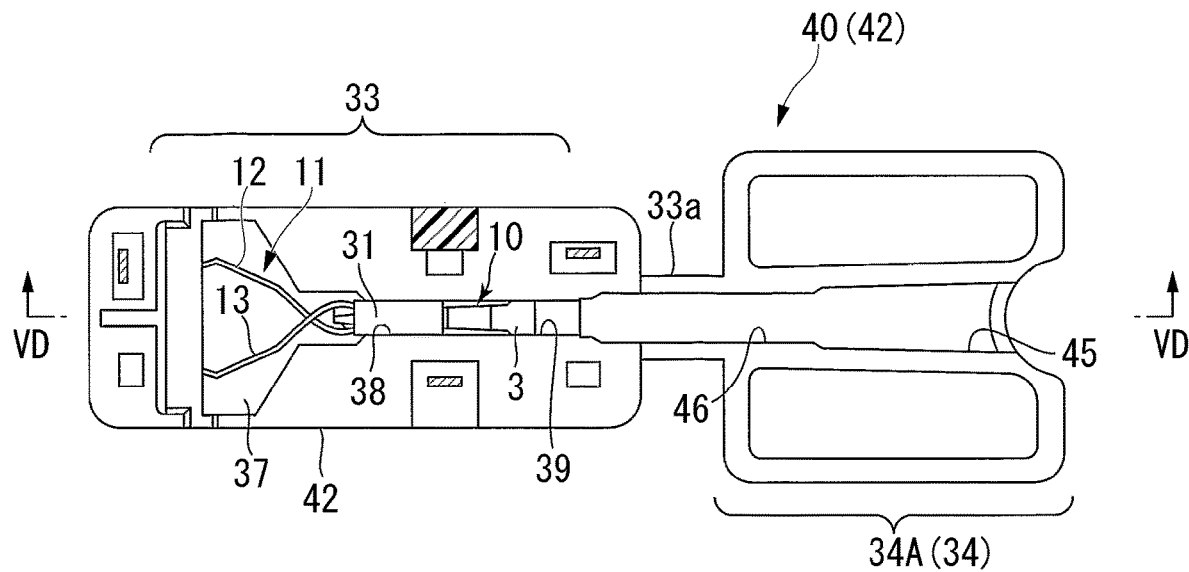
FIG. 5C is a plan view showing the configuration of the lower case of the clip case.
Figure 5D:
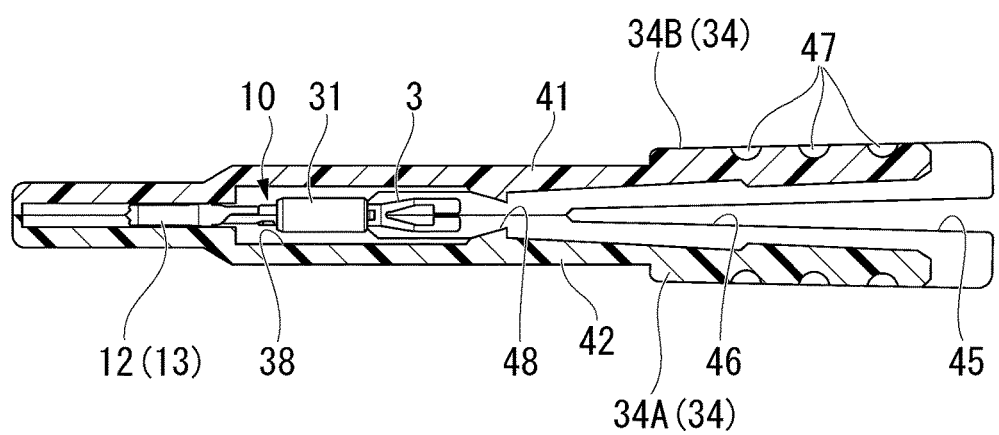
FIG. 5D is a partial cross-sectional view of the clip case in side view.

FIG. 5A is a perspective view schematically showing the configuration of the clip case 40 according to the present embodiment. FIG. 5B is an exploded view schematically showing the configuration of the clip case 40 according to the present embodiment. FIG. 5C is a plan view showing the internal configuration of the lower case 42 of the clip case 40. FIG. 5D is a cross-sectional view showing the configuration of the clip case 40 in side view.

As shown in FIGS. 5A and 5B, the clip case 40 is composed of an upper case 41 having the same shape and the same dimensions, and a lower case 42. The upper case 41 and the lower case 42 can be formed of, for example, various known resin materials having a predetermined hardness and being transparent. The shape of the clip case 40 according to the present embodiment is not particularly limited as long as it can accommodate the clip 10 and is formed in a size that is easy for the operator to hold. For example, the clip case 40 may be formed to have a length of about 50 mm, a width of about 10 to 20 mm, and a thickness of about 5 mm.

As shown in FIG. 5A, the upper case 41 and the lower case 42 of the clip case 40 are connected by engaging the three sets of engaging claws 35 and the engaging holes 36 in correspondence with each other. As shown in FIG. 5B, in a state where the upper case 41 and the lower case 42 of the clip case 40 are connected, inside the cavity 37 formed in a clip accommodating portion 33 formed in the lower case 42, at least the arm member 11 of the clip 10 can be accommodated.

More specifically, as shown in FIGS. 5B to 5D, the arm member 11 of the clip is housed in a cavity 37 formed in the clip accommodating portion 33 of the lower case 42 in an open form in which the first arm 12 and the second arm 13 are separated from each other. The clip accommodating portion 33 is formed with a groove 38 having a depth capable of accommodating the holding tube 31 and the connecting member 3 at a position closer to the proximal end side than the lumen 37. Further, the groove 38 is formed to have an inner diameter such that the proximal end portion 3f of the connecting member 3 can be elastically deformed when the hook 62a tries to enter the notch portion 3g from the proximal end portion 3f of the connecting member 3.

As shown in FIG. 5B, when the clip 10 is housed in the clip accommodating portion 33, the first arm 12 and the second arm 13 of the arm member may abut on the distal end surface in the lumen 37.

As shown in FIGS. 5A and 5B, compression portions 34 that can be pressed by the operator are continuously formed on the proximal end side of the clip accommodating portion 33 in the clip case 40. The compression portion 34 is configured to have a pair of legs 34A and 34B that are separated from each other by a predetermined distance in a state where no external force acts. More specifically, the pair of legs 34A and 34B of the compression portion 34 are formed by being bent at a predetermined angle with respect to the direction of the longitudinal axis of the clip case 40 in a state where no external force acts. That is, the pair of legs 34A and 34B of the compression portion 34 are formed so that the distance between them gradually increases from the distal end side to the proximal end side in a state where no external force acts.

As shown in FIGS. 5B and 5C, the pair of legs 34A and 34B of the compression portion 34 are formed with a groove 46 and an opening 45 continuously formed in the above-mentioned groove 38. The groove 46 is formed on the proximal end side of the groove 38 and has an inner diameter larger than that of the groove 38. Further, the groove 46 is formed by being bent according to the bent shape of the pair of legs 34A and 34B.

In the present embodiment, the groove 38 is formed to have an inner diameter such that the hook 62a, the fixing portion 62b, and the shaft portion 62c can enter and the sheath 66 cannot enter. In other words, the groove 38 is formed to have an inner diameter larger than the width of each of the hook 62a, the fixing portion 62b, and the shaft portion 62c. On the other hand, the groove 46 may be formed having an inner diameter larger than the width of each of the hook 62a, the fixing portion 62b, the shaft portion 62c, and the sheath 66. Further, as shown in FIG. 5D, a stepped portion 48 is formed at the boundary between the groove 38 and the groove 46. Therefore, as will be described later, in the operation of inserting the operation wire 62 into the clip case 40 in order to engage the hook 62a with the connecting member 3, when the sheath 66 is in contact with the stepped portion 48, the hook 62a, the fixing portion 62b and the shaft portion 62c can pass through the groove 46.

In the pair of legs 34A and 34B of the compression portion 34, an opening 45 positioned on the proximal end side of the groove 46 is formed. As shown in FIGS. 5B and 5C, the opening 45 is formed by gradually expanding the inner diameter from the distal end side to the proximal end side. The opening 45 is configured in this way, so that the operation wire 62 can be easily inserted into the clip case 40.

A plurality of hemispherical recesses 47 are formed on the outer peripheral surfaces of the pair of legs 34A and 34B of the compression portion 34. In the present embodiment, these recesses 47 act as anti-slip when compressing the operator compression portion 34. Further, the same effect can be obtained by forming a plurality of protrusions instead of the plurality of hemispherical recesses 47 on the outer peripheral surfaces of the pair of legs 34A and 34B of the compression portion 34.

As described above, the configuration of the lower case 42 of the clip case 40 according to the present embodiment has been described, but since the upper case 42 has the same configuration as the lower case 42, description thereof will be omitted.

(Operation to Load the Clip 10 to the Treatment Tool Main Body 30)

Hereinafter, with reference to FIGS. 6A to 6E, an operation of loading the clip according to the present embodiment to the treatment tool main body 30 will be described as a preparation before treating the target tissue in the body.

First, as shown in FIG. 6A, the operator inserts the treatment tool main body 30 into the clip case 40 until the sheath 66 comes into contact with the stepped portion 48 of the clip case 40. At this time, a part of the operation wire 62 is wound around the shaft portion 103a of the wire adjusting member 103 (see FIG. 4B). Therefore, as shown in FIG. 6A, the hook 62a is housed inside the sheath 66 even when the slider 102 in the operating part 100 is in contact with the distal end surface 101a of the slit 101b. Further, in the wire adjusting member 103, the rotational movement by the knob 103b is restricted by the restricting portion 104.

Next, the operator grasps and compresses the pair of legs 34A and 34B of the compression portion 34 formed on the proximal end side of the clip case 40, so that the compression portion 34 is elastically deformed. As shown in FIG. 6B, since the space between the pair of legs 34A and 34B is compressed, the sheath 66 cannot move forward and backward along the axis C1 direction while being grasped by the pair of legs 34A and 34B.

In this state, the hook 62a is housed inside the sheath 66, similar to the state shown in FIG. 6A. In the operating part 100, the rotational movement of the knob 103b is restricted by the restricting portion 104, and a part of the operation wire 62 is wound around the shaft portion 103a of the wire adjusting member 103.

Figure 6D:
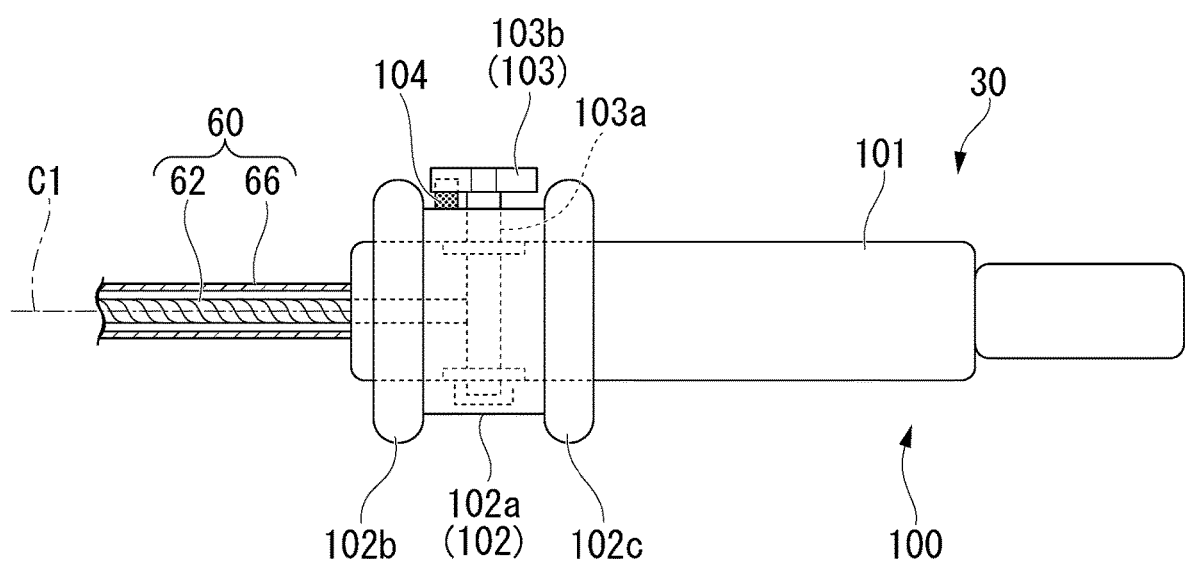
FIG. 6D is a diagram showing an operation of loading a clip unit to a treatment tool main body.

Next, as shown in FIG. 6C, the operator pushes in the restricting portion 104 of the wire adjusting member 103 and rotates the knob 103b counterclockwise. By pushing the restricting portion 104 of the wire adjusting member 103, the restriction on the rotational movement of the knob 103b by the restricting portion 104 is released, and the operator can rotate the knob 103b. In the present embodiment, the operator does not particularly limit the angle at which the knob 103b of the wire adjusting member 103 is rotated counterclockwise. For example, the operator may push in the restricting portion 104 of the wire adjusting member 103 and rotate the knob 103b counterclockwise at a predetermined angle (for example, 90 degrees). At this time, the shaft portion 103a of the wire adjusting member 103 rotates counterclockwise together with the knob 103b, so that a part of the operation wire 62 wound around the shaft portion 103a is released. Further, in the present embodiment, for example, when the operator rotates the knob 103b counterclockwise by 90 degrees, the operation wire 62 wound around the shaft portion 103a may be discharged by about several millimeters. At this time, as shown in FIG. 6D, the operation wire 62 is not wound around the shaft portion 103a of the wire adjusting member 103.

By the above-mentioned operation of the operator, the hook 62a provided on the distal end side of the operation wire 62 advances together with the operation wire 62 and protrudes from the opening on the distal end side of the sheath 66. Further, the hook 62a passes through the hole formed in the proximal end portion 3f of the connecting member 3 and enters the notch portion 3g of the connecting member 3. As a result, as shown in FIG. 6C, the hook 62a is engaged with the notch portion 3g of the connecting member 3, and the operation wire 62 and the clip 10 are connected by the connecting member 3. At this time, the connecting member 3 connecting the operation wire 62 and the clip 10 protrudes from the opening on the distal end side of the sheath 66.

In the process in which the operator pushes the restricting portion 104 and rotates the knob 103b counterclockwise, the knob 103b can pass over the restricting portion 104. At this time, when the operator releases the pressure on the restricting portion 104, the restricting portion 104 protrudes from the surface of the slider 102 and comes into contact with the knob 103b, as shown in FIG. 6D. Therefore, when the operator does not operate the restricting portion 104, the clockwise rotation of the knob 103b is restricted. In other words, the connecting member 3 connecting the operation wire 62 and the clip 10 is maintained in a state of protruding from the opening on the distal end side of the sheath 66.

As shown in FIG. 6C, in a state where the slider 102 is in contact with the distal end surface 101a of the slit 101b (that is, the slider 102 is in the most advanced position) and the hook 62a is protruded from the sheath 66, the distance from the distal end surface of the slider 102 to the distal end of the hook 62a is defined as the first distance from the slider 102 to the hook 62a. In this state, the length of the operation wire 62 from the shaft portion 103a provided in the recess 102a of the slider 102 to the fixing portion 62b connected to the hook 62a is defined as the first length of the operation wire 62.

For convenience of explanation, an example has been described in which the hook 62a is engaged with the notch portion 3g of the connecting member 3 when the slider 102 is advanced along the slit 101b to a position where it abuts on the distal end surface 101a of the slit 101b. However, the present disclosure is not limited to this. For example, in the process in which the slider 102 is advanced along the slit 101b to a position where it abuts on the distal end surface 101a of the slit 101b, it is also possible for the hook 62a to enter and engage with the notch 3g of the connecting member 3 before the slider 102 abuts on the distal end surface 101a. At this time, when the hook 62a enters the notch portion 3g of the connecting member 3 and is engaged, the position of the slider 102 in the operating part 100 in the slit 101b can be regarded as the most advanced position of the slider 102.

As shown in FIGS. 7A and 7B, when the connecting member 3 connecting the operation wire 62 and the clip 10 is positioned outside the sheath 66, the connecting member 3 can rotate in a direction intersecting the axis C1 direction along the direction indicated by the arrow D. Further, when the connecting member 3 is rotated in the direction intersecting the axis C while being positioned outside the sheath 66, the hook 62a can be pulled out from the side of the notch portion 3g of the connecting member 3. On the other hand, when the connecting member 3 is positioned in the sheath 66 in a state where the hook 62a provided at the distal end of the operation wire 62 and the notch portion 3g of the connecting member 3 are engaged with each other, the connecting member 3 is formed to have an inner diameter such that it cannot rotate with respect to the hook 62a. In other words, when the connecting member 3 connecting the clip 10 and the operation wire 62 is positioned in the sheath 66, the sheath 66 maintains the engagement state between the clip 10 and the operation wire 62.

Since the clip 10 and the treatment tool main body 30 according to the present embodiment have the above-described configuration, the used clip 10 can be easily removed from the treatment tool main body 30 and another clip 10 can be replaced. On the other hand, when the clip 10 is loaded to the treatment tool main body 30 and the connecting member 3 protrudes from the opening on the distal end side of the sheath 66, the clip 10 may unintentionally fall off from the treatment tool main body 30.

In order to prevent the clip 10 from being unintentionally dropped from the treatment tool main body 30, as shown in FIG. 6E, after the operator loads the clip 10 to the treatment tool main body 30, the operator operates the wire adjusting member 103 provided on the slider 102. Thereby, at least a part of the connecting member 3 can be housed inside the sheath 66.

More specifically, as shown in FIG. 6E, the operator pushes the restricting portion 104 of the wire adjusting member 103, and rotates the knob 103b clockwise so that the shaft portion 103a of the wire adjusting member 103 can be rotated clockwise. When the operator rotates the knob 103b clockwise, a part of the operation wire 62 is wound around the shaft portion 103a of the wire adjusting member 103, and the hook 62a provided at the distal end of the operation wire 62 and the connecting member 3 engaged with the hook 62a move to the proximal end side with respect to the sheath 66. That is, the clip 10 engaged with the operation wire 62 moves to the proximal end side with respect to the sheath 66. In this process, the slider 102 in the operating part 100 is maintained at the most advanced position in contact with the distal end surface 101a of the slit 101b.

As shown in FIG. 6E, in the present embodiment, when the operator rotates the knob 103b clockwise, at least the connecting member 3 moves to a position closer to the proximal end side than the opening on the distal end side of the sheath 66. In other words, at least the connecting member 3 is housed in the sheath 66. FIG. 6E shows an example in which the proximal end surface of the holding tube 31 is positioned closer to the distal end side than the distal end surface of the sheath 66 and is separated from it, but the proximal end surface of the holding tube 31 may come into contact with the distal end surface of the sheath 66.

In this state, the slider 102 comes into contact with the distal end surface 101a of the slit 101b, so that it cannot move forward any further. Therefore, the hook 62a and the connecting member 3 connected to the operation wire 62 and housed in the sheath 66 do not protrude from the opening on the distal end side of the sheath 66. That is, in the present embodiment, by maintaining the state in which the distance from the slider 102 to the hook 62a is the second distance, it is possible to prevent the clip 10 from being unintentionally dropped from the treatment tool main body 30.

As described above, an example in which the operator rotates the knob 103b clockwise has been described, but the present disclosure is not limited thereto. For example, when the operator pushes in the restricting portion 104 of the wire adjusting portion 103, the restriction on the clockwise rotation operation of the knob 103b by the restricting portion 104 is released. Therefore, the knob 103b may automatically rotate clockwise to return to the initial state shown in FIG. 4A.

In the state shown in FIG. 6E, the operator can return the restricting portion 104 from the pressed position to the initial position (state). That is, the restricting portion 104 is positioned so as to protrude from the recess 102a of the slider 102, and the rotational movement of the knob 103b of the wire adjusting member 103 can be restricted again. As a result, the operation wire 62 is no longer wound around the shaft portion 103a of the wire adjusting portion 103.

As shown in FIG. 6E, in a state where the slider 102 is in contact with the distal end surface 101a of the slit 101b and the engaging portion of the hook 62a and the notch portion 3g of the connecting member 3 is housed in the sheath 66, the distance from the distal end surface of the slider 102 to the distal end of the hook 62a is defined as the second distance from the slider 102 to the hook 62a. In this state, the length of the operation wire 62 from the shaft portion 103a provided in the recess 102a of the slider 102 to the fixing portion 62b connected to the hook 62a is defined as the second length of the operation wire 62. In this embodiment, the second distance and the second length are smaller than the first distance and the first length described above, respectively.

In the present embodiment, unlike the operation of moving the slider 102 forward and backward, the operator rotates the knob 103b of the wire adjusting member 103 clockwise, so that the length of the operation wire 62 from the shaft portion 103a of the wire adjusting member 103 to the fixing portion 62b connected to the hook 62a can be changed from the first length to the second length. In other words, the distance from the slider 102 to the hook 62a can be changed from the first distance to the second distance by the rotational movement of the knob 103b of the wire adjusting member 103. As a result, as will be described later, the engaging portion between the hook 62a and the connecting member 3 can be accommodated inside the sheath 66, and the engaged state between the hook 62a and the connecting member 3 can be maintained.

Figure 6F:
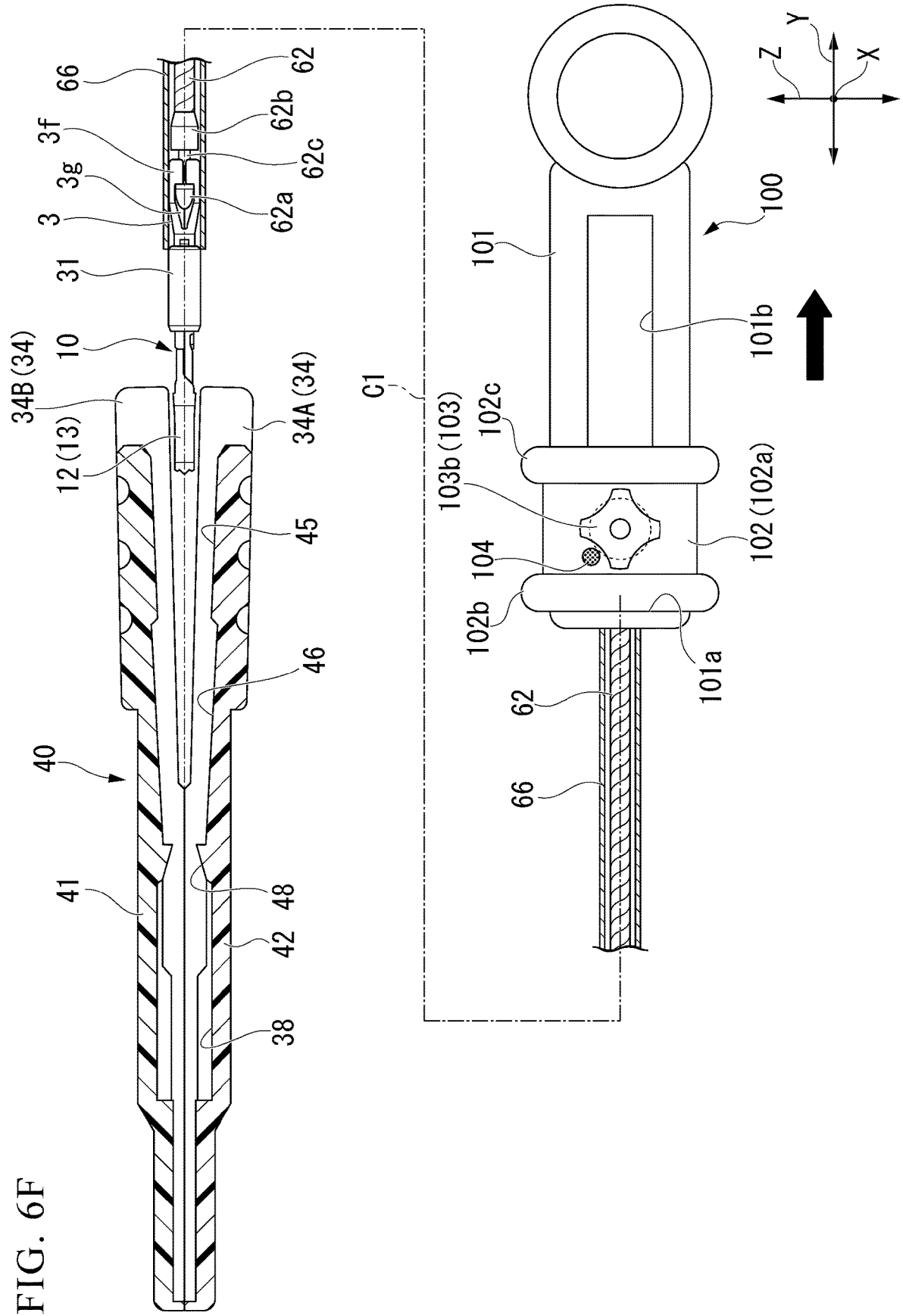
FIG. 6F is a diagram showing an operation of loading a clip unit to the treatment tool main body.

After that, as shown in FIG. 6F, in a state where the engagement between the clip 10 and the operation wire 62 is maintained, the operator releases the compressive force on the compression portion 34 of the clip case 40, and grasps the operating part 100 and removes the insertion portion 60 of the treatment tool main body 30 to which the clip 10 is loaded from the clip case 40. In this process, the operator does not need to pull the slider 102 back to the proximal end side. That is, the state in which the slider 102 is in contact with the distal end surface 101a of the slit 101b is maintained. The proximal end surface of the holding tube 31 is in contact with the distal end surface of the sheath 66.

By this operation, the clip 10 according to the present embodiment can be loaded to the treatment tool main body 30.

(Procedure by Medical Apparatus 1)

Hereinafter, a procedure for ligating the target tissue T using the medical apparatus 1 according to the present embodiment having the above-described configuration will be described with reference to FIGS. 8 to 11.

As shown in FIG. 8, when the clip 10 is taken out from the clip case 40 in a state of being loaded to the treatment tool main body 30, the first arm 12 and the second arm 13 of the arm member 11 of the clip 10 become an open state separated from each other by their own elastic restoring force. In this state, the slider 102 is in the most advanced position of the operating part 100 on the proximal end side in contact with the distal end surface 101a of the slit 101b, and the restricting portion 104 restricts the rotational movement of the knob 103b of the wire adjusting member 103.

The elastic restoring force of the first arm 12 and the second arm 13 of the arm member 11 of the clip 10 moves the holding tube 31 toward the proximal end side. Therefore, as shown in FIG. 8, the holding tube 31 is in contact with the distal end of the sheath 66. However, since the holding tube 31 has an outer diameter larger than the inner diameter of the sheath 66, it does not enter the sheath 66.

The operator inserts an endoscope (not shown) into the patient's body. Then, the operator can insert the medical apparatus 1 from the proximal end of the endoscope channel and protrude the medical apparatus 1 from the distal end of the endoscope channel. In this process, a closed state is maintained in which the first arm 12 and the second arm 13 of the arm member 11 are closed by an operation such as the operator continuing to hold the slider 102. At that time, a part of the intermediate portion 14 positioned on the proximal end side of the arm member 11 is positioned in the large diameter portion 31c of the holding tube 31.

When the operator guides the medical apparatus 1 through the channel of the endoscope to the vicinity of the target tissue T, the arm member 11 is changed from the closed state to the open state as shown in FIG. 8. At this time, the slider 102 is in contact with the distal end surface 101a of the slit 101b and is in the most advanced position. Further, the proximal end surface of the holding tube 31 comes into contact with the distal end surface of the sheath 66.

In the state shown in FIG. 8, the operator can confirm the size of the target tissue T and the opening width of the arm member 11. For example, when the opening width of the arm member 11 (the width between the first arm 12 and the second arm 13) is smaller than the size of the target tissue T, the operator operates the operating part 100 to adjust the opening width of the arm member 11.

Figure 9:
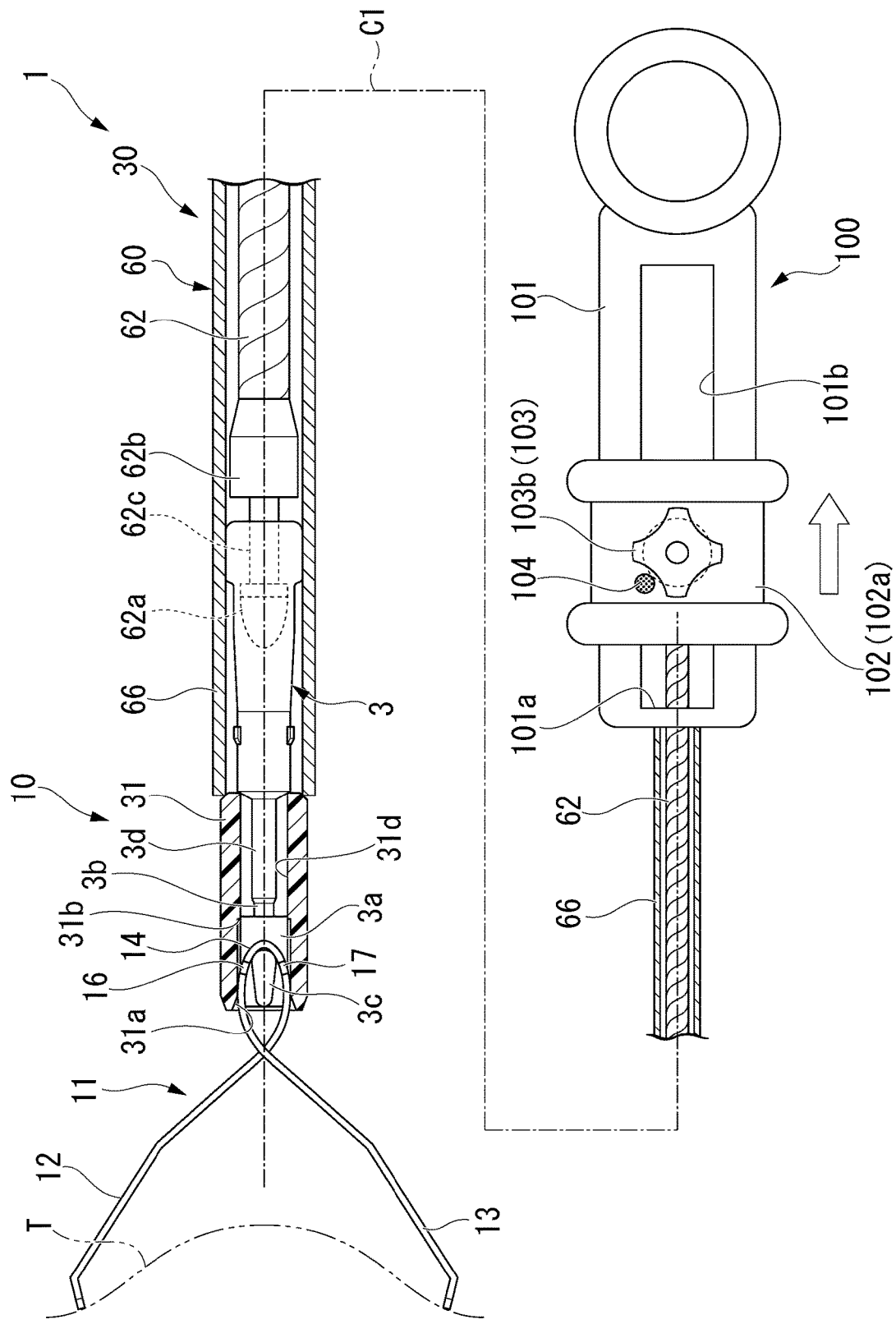
FIG. 9 is a diagram showing an operation of treating a target tissue using the medical apparatus.

More specifically, in the present embodiment, when the operator moves the slider 102 of the operating part 100 forward and backward, the clip 10 moves forward and backward together with the operation wire 62. That is, the first arm 12 and the second arm 13 of the arm member 11 of the clip 10 can move relative to the holding tube 31 by moving back and forth together with the operation wire 62. As a result, the first arm 12 and the second arm 13 of the arm member 11 are in contact with the tapered surface 31a provided on the distal end side of the holding tube 31, and the opening width of the arm member 11 between them is expanded or decreased. As shown in FIG. 8, for example, when the operator pulls the slider 102 slightly toward the proximal end side, in the arm member 11, the intermediate portion 14 (the portion on the proximal end side of the intersection of the first arm 12 and the second arm 13) enters the large diameter portion 31c of the holding tube 31, and the first arm 12 and the second arm 13 are separated from each other in the radial direction of the arm member 11. As a result, as shown in FIG. 9, the operator can expand (adjust) the opening width of the arm member 11 according to the size of the target tissue T.

In this process, the pair of protrusions 16 and 17 provided on the proximal end side of the arm member 11 are positioned in the large diameter portion 31c on the distal end side of the stepped portion 31b in the holding tube 31, so as not to cut into the inner wall of the holding tube 31. Therefore, when the operator pushes the slider 102 toward the distal end side, the arm member 11 can be moved toward the distal end side and the distance between the first arm 12 and the second arm 13 can be adjusted.

After that, the operator can operate an endoscope (not shown), adjust the direction and orientation of the arm member 11 of the clip 10, and press the arm member 11 toward the target tissue T. As shown in FIG. 9, by this operation, the target tissue T can be positioned between the first arm 12 and the second arm 13 of the arm member 11 in the open state. When the operator confirms that the target tissue T is positioned between the first arm 12 and the second arm 13, the operator operates the endoscope to hold the target tissue T by the first arm 12 and the second arm 13 of the arm member 11.

After confirming that the target tissue T is positioned between the first arm 12 and the second arm 13, the operator grasps the operating part main body 101 and pulls back the slider 102. At this time, the operation wire 62 and the first arm 12 and the second arm 13 move together with each other toward the proximal end side. In a state where the intersection of the first arm 12 and the second arm 13 has entered the holding tube 31, the first arm 12 and the second arm 13 come into contact with the tapered surface 31a provided on the distal end side of the holding tube 31. Then, the first arm 12 is elastically deformed to the second arm 13 side, and the second arm 13 is elastically deformed to the first arm 12 side. As a result, the distal end of the first arm 12 and the distal end of the second arm 13 come close to each other, and the opening width of the arm member 11 is reduced, so that the arm member 11 transitions from the open state to the closed state.

Figure 10:
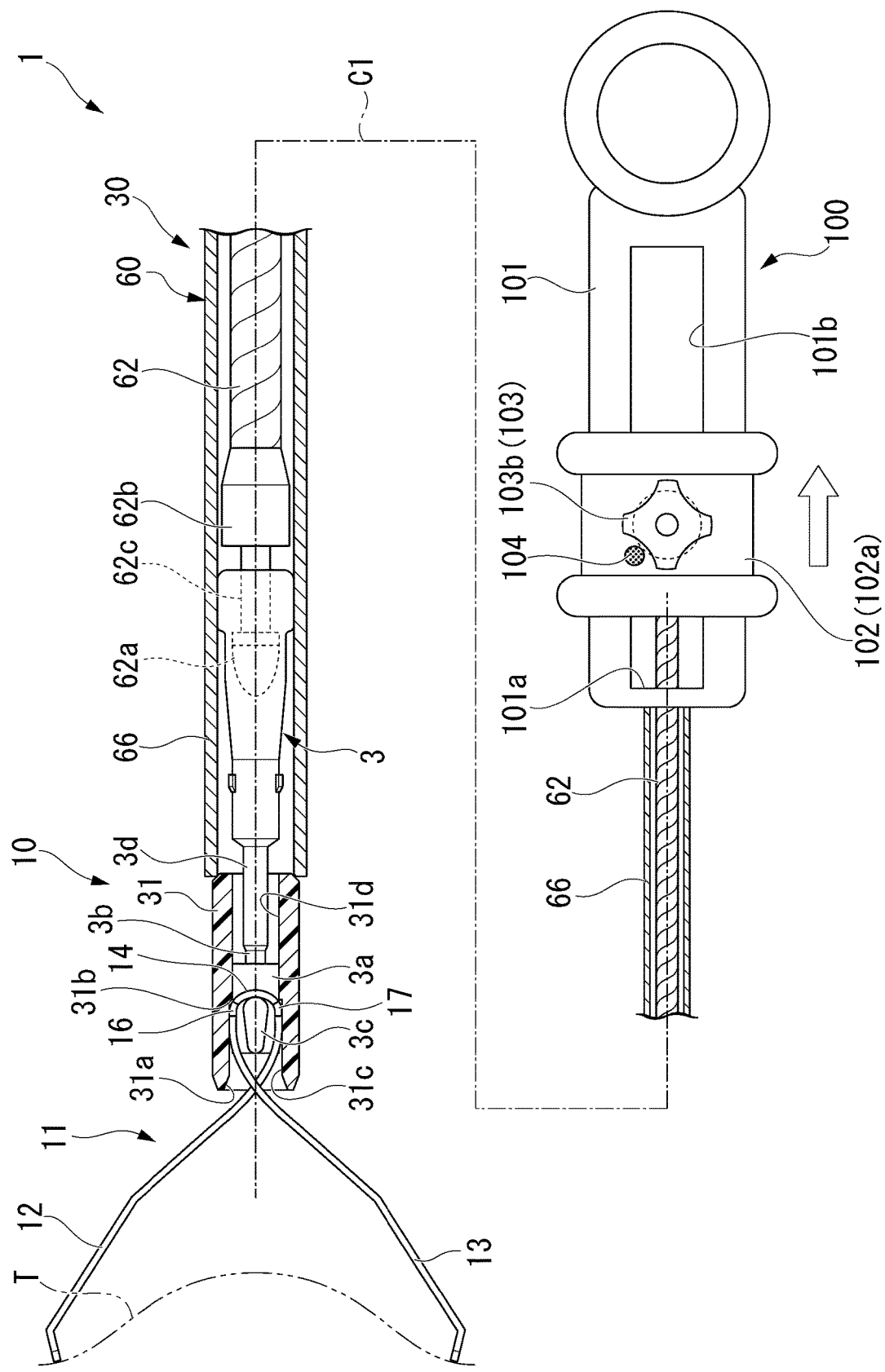
FIG. 10 is a diagram showing an operation of treating a target tissue using the medical apparatus.

As shown in FIGS. 9 and 10, in the process of the operator pulling the slider 102 back to the proximal end side, the proximal end portion of the arm member 11 including the intermediate portion 14 is pulled back to the proximal end side in the holding tube 31. In the present embodiment, the operator pushes the slider 102 toward the distal end until the pair of protrusions 16 and 17 provided at the proximal end portion of the arm member 11 abuts on the stepped portion 31b in the holding tube 31. Thereby, the arm member 11 can be moved to the distal end side. In other words, the arm member 11 can be transitioned to the open state by the operator pushing the slider 102 toward the distal end until the pair of protrusions 16 and 17 on the arm member 11 abut on the stepped portion 31b. By this operation, the operator can re-grasp the target tissue T by using the arm member 11.

That is, in the process of pulling the slider 102 back to the above-mentioned state, the clip 10 can be made to face the target tissue T again by the operator operating the endoscope. After that, the target tissue T can be re-grasped with the clip 10 by the above-mentioned procedure.

When the operator confirms that the target tissue T is held by the arm member 11 in the closed state in a desired state, the slider 102 can be pulled back to the proximal end side until the pair of protrusions 16 and 17 provided on the arm member 11 pass over the stepped portion 31b in the holding tube 31 and are positioned in the small diameter portion 31d. In this state, the pair of protrusions 16 and 17 bite into the inner wall of the small diameter portion 31d of the holding tube 31 to prevent the arm member 11 from moving toward the distal end side with respect to the holding tube 31. In other words, when the pair of protrusions 16 and 17 provided on the arm member 11 are positioned on the small diameter portion 31d of the holding tube 31, the state in which the arm member 11 in the closed state holds the target tissue T is maintained. As shown in FIG. 11A, a state where the root of the target tissue T is bound by the first arm 12 and the second arm 13 and the distance between the first arm 12 and the second arm 13 is substantially zero is also included in the closed state of the arm member 11.

In this state, the engaging portion between the hook 62a and the connecting member 3 is moved to the proximal end side in the sheath 66. As shown in FIG. 11A, when the pair of protrusions 16 and 17 provided on the arm member 11 are pulled back to a position protruding from the opening on the proximal end side of the holding tube 31, they come into contact with and engage with the proximal end surface of the holding tube 31. That is, even if the force for moving the arm member 11 to the proximal end side of the holding tube 31 is released, the pair of protrusions 16 and 17 are locked to the distal end side with respect to the proximal end surface of the holding tube 31. The arm member 11 is restricted from moving toward the distal end side with respect to the holding tube 31, and the state of holding the target tissue T in the closed state is locked. In this state, the hook portion 3c hooked on the intermediate portion 14 of the arm member 11 is positioned on the proximal end side of the opening on the proximal end side of the holding tube 31, and is positioned in the sheath 66.

After this, the operator separates the clip 10 ligating the target tissue T from the treatment tool body 30. Specifically, the operator pulls the slider 102 back to the proximal end side in a locked state in which the pair of protrusions 16 and 17 are locked to the proximal end surface of the holding tube 31 toward the proximal end side. Thereby, when the amount of operating force of the slider 102 reaches a predetermined value or more, the amount of tensile force acting on the small diameter portion 3b of the connecting member 3 exceeds the tensile strength at which the small diameter portion 3b breaks. At this time, the small diameter portion 3b is broken, and as shown in FIG. 11B, the connecting member 3 is placed in the body in a state where a distal end portion 3a, a hook portion 3c, and a part of the small diameter portion 3b are connected to the arm member 11. On the other hand, a part of the small diameter portion 3b, the medium diameter portion 3d, the large diameter portion 3e, the notch portion 3g, the proximal end portion 3f, and the protrusion portion 3h are positioned in the sheath 66 in a state of being engaged with the hook 62a. Further, the arm member 11 of the clip 10 binds the target tissue T in a closed state in which the opening widths of the first arm 12 and the second arm 13 are substantially zero. When the small diameter portion 3b is broken, the clip 10 to which the target tissue T is ligated is placed in the body.

After the clip 10 ligated with the target tissue T is placed in the body, the operator can operate the endoscope and take out the medical apparatus 1 from the channel of the endoscope. After that, the operator takes necessary measures and completes a series of procedures.

(Reloading of Clip 10)

In the present embodiment, the operator can treat another target tissue T using the medical apparatus 1 by loading the new clip 10 to the treatment tool main body 30.

Specifically, the operator pushes the slider 102 toward the distal end side until the slider 102 abuts on the distal end surface 101a of the slit 101b. After that, the restricting portion 104 provided on the slider 102 is pushed in, and the knob 103b of the wire adjusting member 103 is rotated counterclockwise to release the operation wire 62 wound around the shaft portion 103a of the wire adjusting member 103.

By this operation, the length of the operation wire 62 from the shaft portion 103a of the wire adjusting member 103 to the fixing portion 62b connected to the hook 62a is changed from the second length to the first length. As a result, the distance from the distal end surface of the slider 102 to the distal end of the hook 62a is changed from the second distance to the first distance. In this state, the operator protrudes a part of the connecting member 3 engaged with the hook 62a from the opening on the distal end side of the sheath 66.

Then, by the operation shown in FIGS. 7A and 7B described above, the operator removes a part of the connecting member 3 from the hook 62a, and then sterilizes the treatment tool main body 30 as necessary. The new clip 10 can be loaded to the treatment tool main body 30 by the procedure shown in 1.

(Effect of Medical Apparatus 1)

According to the medical apparatus 1 of the present embodiment, the wire adjusting member 103 is arranged on the slider 102 of the operating part 100 on the proximal end side. The operator can change the distance from the slider 102 to the hook 62a by operating the wire adjusting member 103 in a state where the slider 102 is in contact with the distal end surface 101a of the slit 101b by pushing the slider 102.

More specifically, in a state where the slider 102 is in contact with the distal end surface 101a of the slit 101b and is in the most advanced position, when the operator pushes in the restricting portion 104 and rotates the knob 103b of the wire adjusting member 103 counterclockwise, the distance from the slider 102 to the hook 62a is changed from the second distance to the first distance. As a result, the hook 62a can be protruded from the opening on the distal end side of the sheath 66 without the operator moving the slider 102 forward and backward. In this state, it is possible to remove the used clip 10 and load a new clip 10 to the treatment tool main body 30. Therefore, according to the medical apparatus 1 of the present embodiment, the clip 10 can be reloadable.

Further, in a state where the slider 102 is in contact with the distal end surface 101a of the slit 101b and is in the most advanced position, when the operator pushes the restricting portion 104, the knob 103b of the wire adjusting member 103 rotates clockwise to return to the initial state. By this operation, the distance from the slider 102 to the hook 62a is changed from the above-mentioned first distance to a second distance smaller than the first distance. As a result, even if the operator moves the slider 102 forward and backward, the hook 62a does not protrude from the opening on the distal end side of the sheath 66. In this state, even if the operator moves the slider 102 to the most advanced position, the engaging portion between the hook 62a and the notch portion 3g of the connecting member 3 does not protrude from the opening on the distal end side of the sheath 66. Therefore, when the operator treats the target tissue T using the medical apparatus 1 according to the present embodiment, even if the slider 102 is moved to the most advanced position due to an erroneous operation, the engagement between the hook 62a and the notch portion 3g of the connecting member 3 is not unintentionally released.

Further, according to the medical apparatus 1 of the present embodiment, the operator can advance/retract the slider 102 to advance/retract the arm member 11 together with the operation wire 62 with respect to the holding tube 31. In the present embodiment, the first arm is moved by the operator moving the slider 102 forward and backward until the pair of protrusions 16 and 17 formed on the proximal end side of the arm member 11 abut on the stepped portion 31b of the holding tube 31. Thereby, the opening width between the 12 and the second arm 13 can be readjusted. In other words, according to the medical apparatus 1 of the present embodiment, in the re-grasping operation of the target tissue T using the arm member 11, the engagement between the hook 62a and the notch portion 3g of the connecting member 3 is not unintentionally released.

Based on the above, according to the medical apparatus 1 of the present embodiment, it is possible to achieve both the reloadability of the clip 10 and the re-grasping operation of the target tissue T with respect to the treatment tool main body 30.

According to the medical apparatus 1 of the present embodiment, the wire adjusting member 103 has a simple configuration including a shaft portion 103a and a knob 103b, and is easy to manufacture. Therefore, the medical apparatus 1 can be configured at low cost.

Hereinafter, the medical apparatus 2 according to another exemplary embodiment of the present disclosure will be described with reference to FIGS. 12A to 15C. Hereinafter, description of the same configuration as that of the endoscope clip 1 according to the above embodiment will be omitted, and the points different from those of the above embodiment will be mainly described.

Figure 12A:
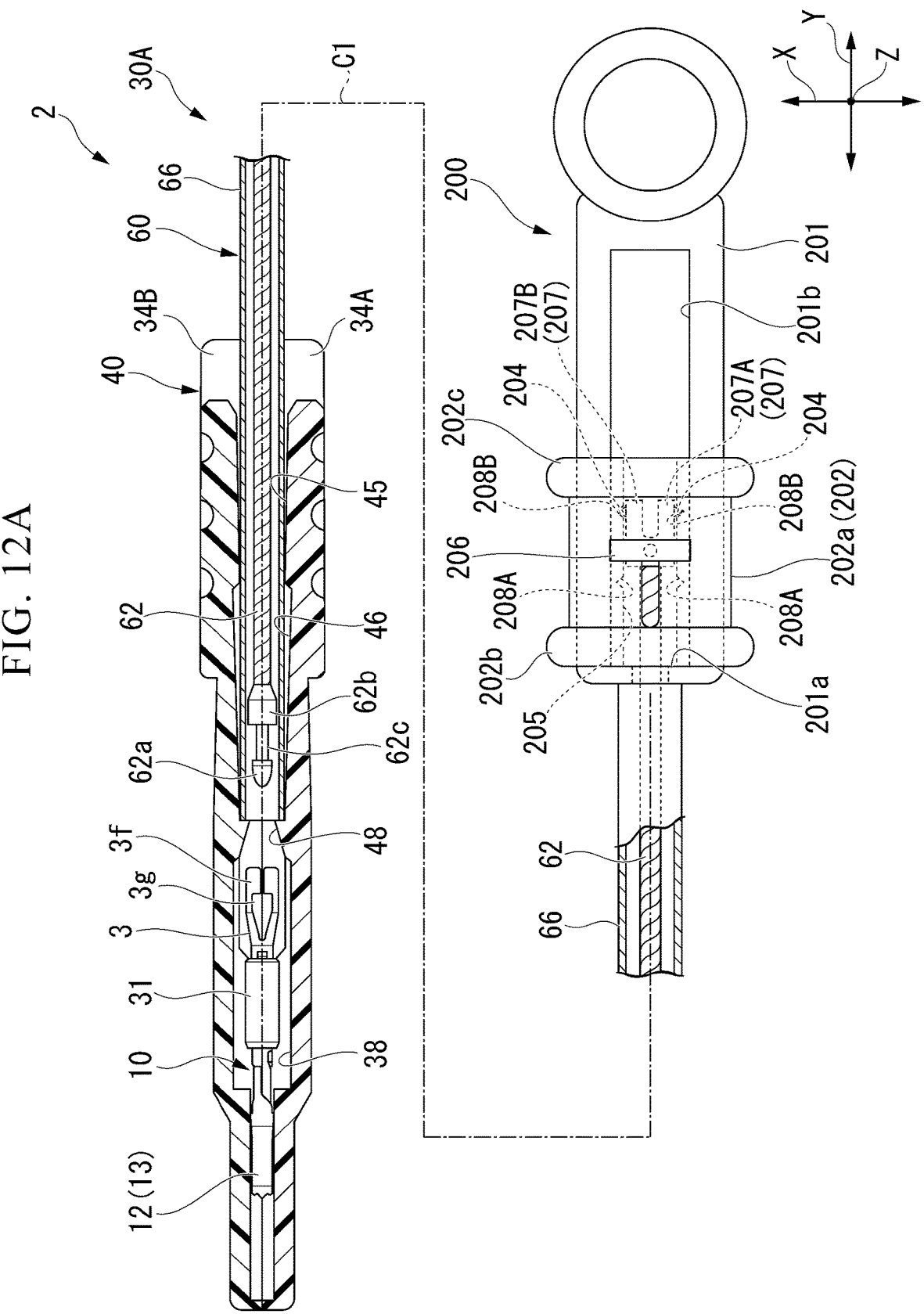
FIG. 12A is a partial cross-sectional view schematically showing a configuration of a medical apparatus according to an exemplary embodiment of the present disclosure.
Figure 12B:
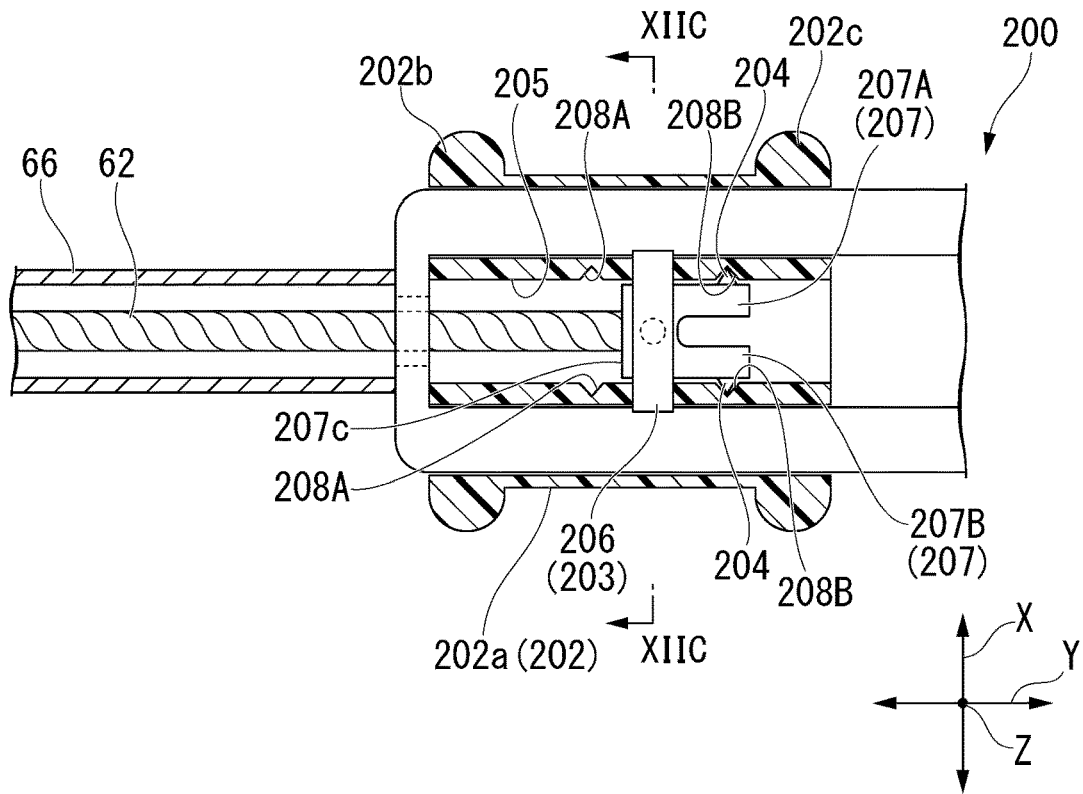
FIG. 12B is an enlarged cross-sectional view schematically showing a configuration of an applicator of the medical apparatus.
Figure 12C:
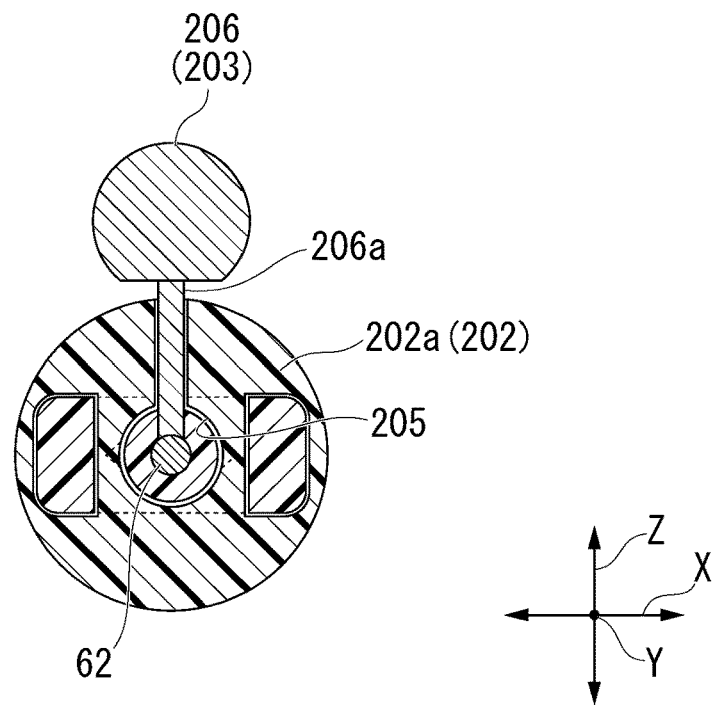
FIG. 12C is a radial cross-sectional view of an applicator viewed from the proximal end side of the medical apparatus along XIIC-XIIC in FIG. 12B.
Figure 12D:
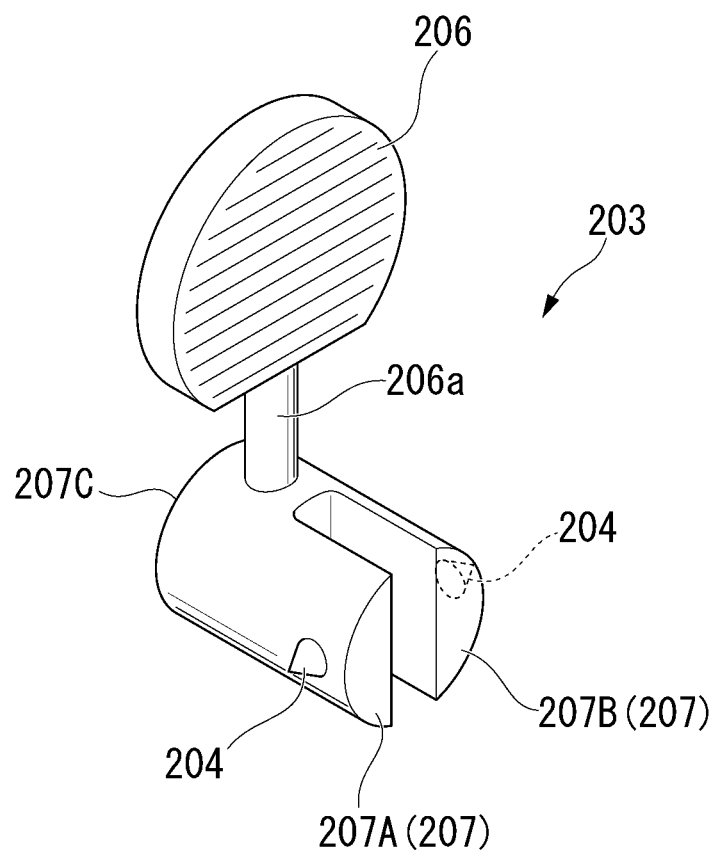
FIG. 12D is a perspective view schematically showing a configuration of a part of an operating part of the medical apparatus.

FIG. 12A is a partial cross-sectional view schematically showing the configuration of the medical apparatus 2. FIG. 12B is an enlarged cross-sectional view schematically showing a partial configuration of the medical apparatus 2. FIG. 12C is a radial cross-sectional view taken from the proximal end side of the medical apparatus 2 along XIIC-XIIC in FIG. 12B. FIG. 12D is a perspective view showing the configuration of the wire adjusting member 203 in the medical apparatus 2 according to the present embodiment. FIGS. 13A to 15C are diagrams showing an operation of treating the target tissue T using the medical apparatus 2 according to the present embodiment.

As shown in FIG. 12A, the medical apparatus 2 according to the present embodiment is configured to have an operating part 200 instead of the operating part 100 as compared with the medical apparatus 1 according to the embodiment described above with respect to FIGS. 1-11B. More specifically, the medical apparatus 2 has a wire adjusting member 203 having a configuration different from that of the wire adjusting member 103 of the medical apparatus 1 according to the embodiment described above.

Since the other configurations of the medical apparatus 2 according to the present embodiment are the same as those of the medical apparatus 1 according to the embodiment described above, the same reference numerals are given in the drawings, and description thereof will be omitted.

As shown in FIGS. 12A and 12B, in the slider (first operating part) 202 of the operating part 200 of the medical apparatus 2, the lumen 205 is formed along the direction of the axis C1. The medical apparatus 2 has a wire adjusting member (second operating part) 203 composed of a main body 207, a knob 206, and two protrusions 204. As shown in FIG. 12B, a part of the inner wall of the slider 202 is cut out along the direction of the axis C1 within the range where the cavity 205 of the slider 202 is formed. Thereby, a pair of distal end end recesses 208A and a pair of proximal end recesses 208B are formed. Along the direction of the axis C1, the pair of distal end recesses 208A are positioned closer to the distal end than the pair of proximal end recesses 208B.

The main body 207 of the wire adjusting member 203 is a hollow tube-shaped member having an outer diameter smaller than the inner diameter of the lumen 205. That is, the main body 207 can be inserted into the cavity 205 formed in the slider 202. The main body 207 can be configured by using, for example, a resin material having a predetermined rigidity. A pair of tail portions 207A and 207B are formed by cutting off a part of the main body 207 on the proximal end side. Further, as will be described later, in order to connect the operation wire 62 to the wire adjusting member 203, a hole (not shown) into which the operation wire 62 can be inserted is formed on the distal end side of the main body 207.

In the pair of tail portions 207A and 207B of the main body 207, a pair of protrusions 204 protruding radially outward from the outer peripheral surface are formed. The pair of protrusions 204 can enter and engage with the distal end recess 208A and the proximal end recess 208B. In the present embodiment, the method of forming the pair of protrusions 204 on the main body 207 is not particularly limited. For example, the pair of protrusions 204 may be formed by adhering to the pair of tail portions 207A and 207B of the main body 207, or may be formed integrally with the main body 207.

In the present embodiment, as shown in FIG. 12D, an example in which a pair of protrusions 204 are formed in a conical shape will be described, but the present disclosure is not limited thereto. The pair of protrusions 204 may be engaged with the proximal end recess 208B or the distal recess 208A formed in the lumen 205 of the slider 202, and the specific shape is not particularly limited. Further, in the present embodiment, examples will be described in which the pair of distal end recesses 208A and the pair of proximal end recesses 208B formed in the cavity 205 are positioned at two locations on the inner wall of the cavity 205 of the slider 202 according to the shape of the pair of protrusions 204, but the present disclosure is not limited to this. For example, in the cavity 205 of the slider 202, the distal end recess 208A and the proximal end recess 208B may be formed all around the inner wall of the slider 202 in the circumferential direction.

The wire adjusting member 203 has a knob 206 formed on the outer peripheral surface of the main body 207 on the distal end side. The knob 206 can be moved forward and backward with respect to the slider 202 by moving forward and backward while being grasped by the operator. The knob 206 may be integrally formed of the same material as the main body 207, or may be formed with the main body 207 and then connected by the shaft portion 206a. As shown in FIG. 12D, for example, an uneven pattern may be formed on the distal end surface and the proximal end surface of the knob 206 to prevent slipping.

As shown in FIGS. 12B and 12C, the proximal end of the operation wire 62 is inserted and fixed in a hole (not shown) formed on the distal end side of the main body 207. In the present embodiment, the proximal end of the operation wire 62 may be fixed to the main body 207, and the shape of the hole formed on the distal end side of the main body 207 is not particularly limited. For example, it may be a hole that penetrates the main body 207 in the direction of the axis C1, or may not penetrate the main body 207. Further, the proximal end of the operation wire 62 may be fixed to the distal end surface 207C of the main body 207. The method of fixing the operation wire 62 to the main body 207 is not particularly limited. The proximal end of the operation wire 62 can be fixed to the main body 207 by various known methods such as brazing and bonding with an adhesive. Therefore, when the operator moves the main body 207 forward and backward with respect to the slider 202, the operation wire 62 can move forward and backward with respect to the slider 202 together with the main body 207.

According to the wire adjusting member 203 of the present embodiment, the operator grasps the knob 206 and moves (slides) the main body 207 along the direction of the axis C1. Thereby, the wire adjusting member 203 can be inserted into or pulled out from the cavity 205. In other words, the distance from the distal end of the slider 202 to the distal end of the hook 62a can be adjusted by operating only the wire adjusting member 203 without operating the slider 202.

More specifically, in the present embodiment, as shown in FIG. 12A, in the state where the slider 202 is in contact with the most advanced position in the slit 201b of the operating part main body 201, that is, the distal end surface 201a of the slit 201b, when the pair of protrusions 204 of the body 207 are engaged into the proximal end recess 208B in the lumen 205 of the slider 202, the distance from the distal end surface of the slider 202 to the distal end of the hook 62a is the second distance between the slider 202 and the hook 62a. Then, in a state where the slider 202 is in contact with the distal end surface 201a in the slit 201b, when the pair of protrusions 204 of the body 207 are engaged into the distal end recess 208A in the lumen 205 of the slider 202, the distance from the distal end surface of the slider 202 to the distal end of the hook 62a is the first distance between the slider 202 and the hook 62a (see FIG. 13A). In other words, in the present embodiment, the distance between the slider 202 and the hook 62a can be adjusted to the first distance and the second distance only by operating the wire adjusting member 203 without operating the slider 202.

In this embodiment, the first distance between the slider 202 and the hook 62a is larger than the second distance. Further, similarly to the embodiment described above with respect to FIGS. 1 to 11B, in a state where the distance between the slider 202 and the hook 62a is the first distance, when the hook 62a protrudes from the opening on the distal end side of the sheath 66 and the hook 62a is the second distance, the hook 62a is positioned on the proximal end side of the opening on the distal end side of the sheath 66, that is, in a position where the hook 62a is housed in the sheath 66. Therefore, in the present embodiment, in the state where the slider 202 is in contact with the most advanced position in the slit 201b of the operating part main body 201, that is, the distal end surface 201a of the slit 201b, the hook 62a can be protruded from the opening on the distal end side of the sheath 66, and the hook 62a can be accommodated in the sheath 66, by the operator simply operating the wire adjusting member 203 without operating the slider 202.

When the operator operates the wire adjusting member 203, the operation wire 62 moves forward and backward together with the operation wire 62 and the wire adjusting member 203, so that the operation wire 62 moves back and forth relative to the slider 202. However, since the proximal end of the operation wire 62 is fixed to the wire adjusting member 203, the length of the operation wire from the position where the operation wire 62 is fixed to the main body 207 of the wire adjusting member 203 to the fixing portion 62b connected to the hook 62a along the direction of the axis C1 is constant.

When the operator does not operate the wire adjusting member 203, the pair of protrusions 204 are engaged with the cavity 205 formed in the slider 202, so that the wire adjusting member 203 and the slider 202 can be maintained in a relatively immovable state. In this state, when the operator moves the slider 202 forward and backward, the wire adjusting member 203 moves forward and backward together with the slider 202.

(Operation of Medical Apparatus 2)

Hereinafter, the operation of the medical apparatus 2 according to the present embodiment will be described with reference to FIGS. 12A to 15C. Specifically, the operation of loading the clip 10 in the medical apparatus 2 to the treatment tool main body 30A will be described with reference to FIGS. 12A to 13C. A procedure for ligating the target tissue T using the medical apparatus 2 will be described with reference to FIGS. 14 to 15C.

As shown in FIGS. 12A and 12B, when the clip 10 in the medical apparatus 2 is loaded to the treatment tool main body 30A, the operator first grasps the operating part 200, and inserts the treatment tool main body 30A into the clip case 40 until the sheath 66 comes into contact with the stepped portion 48 of the clip case 40. At this time, the hook 62a is housed inside the sheath 66. On the other hand, in the operating part 200, in the wire adjusting member 203, a pair of protrusions 204 of the main body 207 are engaged with the proximal end recess 208B in the cavity 205 of the slider 202. Further, the slider 202 is in the most advanced position in the slit 201b in contact with the distal end surface 201a. In this state, the distance between the slider 202 of the operating part 200 and the hook 62a is the second distance.

Figure 13A:
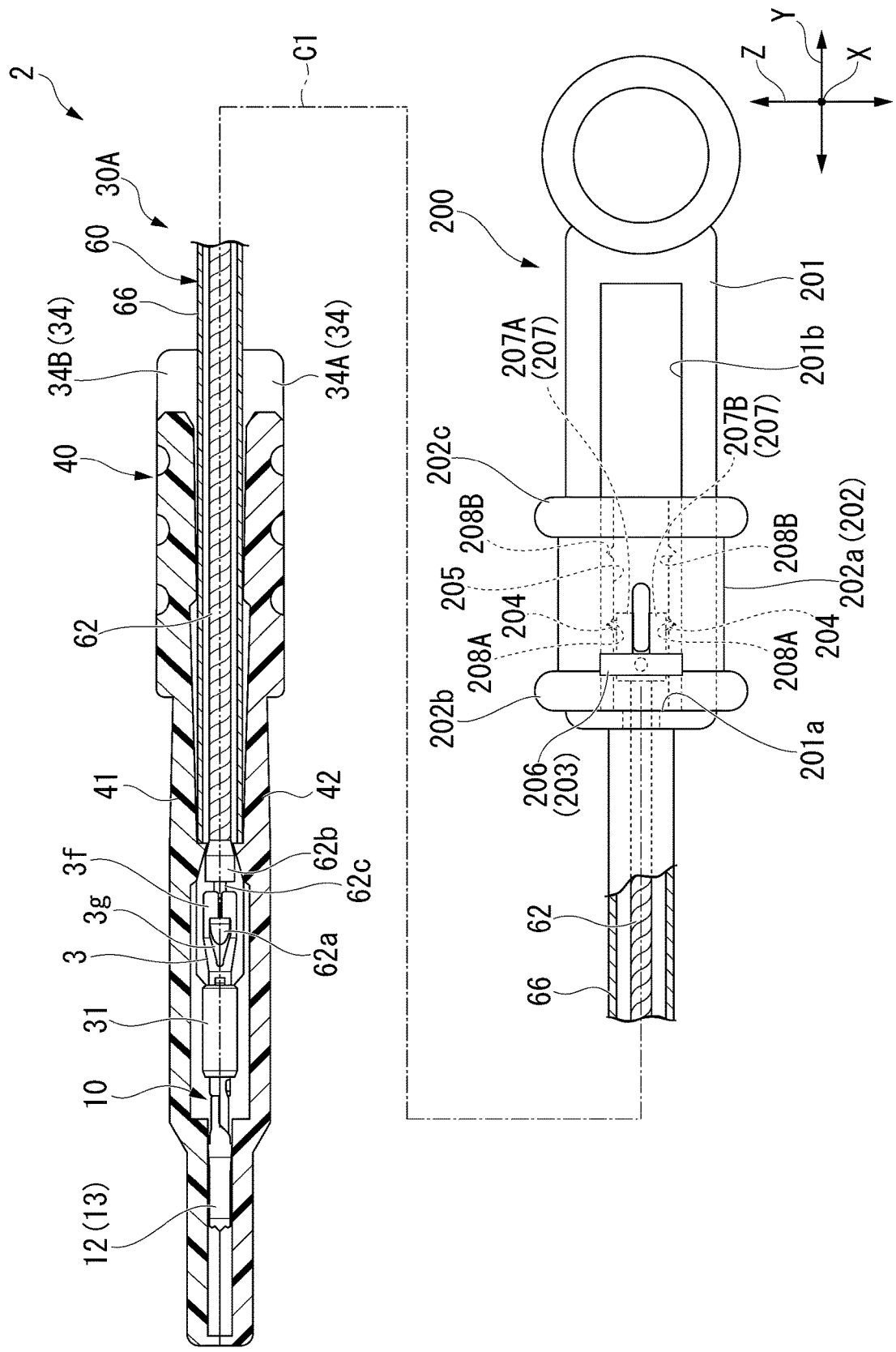
FIG. 13A is a diagram showing an operation of treating a target tissue using the medical apparatus.

Next, as shown in FIG. 13A, the operator grasps and compresses the pair of legs 34A and 34B of the compression portion 34 of the clip case 40 so that the sheath 66 is grasped in a state where the position with respect to the clip case 40 is fixed. In this state, the operator grasps the knob 206 of the wire adjusting member 203 and moves (slides) the main body 207 toward the distal end side along the axis C1 direction. By this operation of the operator, the pair of protrusions 204 engaged with the proximal end recess 208B of the lumen 205 of the slider 202 attempts to move to the distal end side in a state of abutting and pressing against the inner wall of the proximal end recess 208B. Then, the repulsive force from the inner wall of the proximal end recess 208B acts on the pair of protrusions 204 and the pair of tail portions 207A and 207B of the wire adjusting member 203, so that the pair of tail portions 207A and 207B are pressed inward in the radial direction of the operating part 200. As a result, the distance between the pair of tail portions 207A and 207B is reduced and they come closer to each other. In other words, the pair of tail portions 207A and 207B formed on the main body 207 of the wire adjusting member 203 are in a bent state, and the width of the main body 207 on the proximal end side in the radial direction is reduced.

As a result, the wire adjusting member 203 can move the pair of protrusions 204 of the main body 207 toward the distal end side with respect to the slider 202 in the lumen 205 by overcoming the proximal end recess 208B. When the operator moves the knob 206 of the wire adjusting member 203 to the distal end side while grasping it, in a state where the pair of tail portions 207A and 207B are bent, the wire adjusting member 203 is moved toward the distal end side with respect to the slider 202 until the pair of protrusions 204 enter and engage with the distal end recess 207A formed in the cavity 205. At this time, the pair of tail portions 207A and 207B return to a state of being separated from each other by the elastic restoring force.

In this process, the operation wire 62 fixed to the main body 207 of the wire adjusting member 203 and the hook 62a connected to the distal end side of the operation wire 62 are moved together with respect to the distal end side with respect to the slider 202. As a result, as shown in FIG. 13A, the hook 62a protrudes from the distal end side opening of the sheath 66 and enters the notch portion 3g of the connecting member 3, so that the hook 62a and the connecting member 3 engage with each other. At this time, the distance between the slider 202 of the operating part 200 and the hook 62a changes from the second distance to the first distance larger than the second distance. On the other hand, since the operator has not operated the slider 202, the state in which the slider 202 is in contact with the distal end surface 201a in the slit 201b is maintained.

Next, the operator does not operate the slider 202, grasps the knob 206 of the wire adjusting member 203, and slides the main body 207 toward the proximal end side along the axis C1 direction. By this operation, the pair of protrusions 204 of the main body 207 are moved over the distal end recess 208A in the cavity 205 to the proximal end side while maintaining the state in which the slider 202 is in contact with the distal end surface 201a of the slit 201b. As a result, as shown in FIG. 13B, the wire adjusting member 203 is moved to the proximal end side until the pair of protrusions 204 enter and engage with the proximal end recess 208B. In the present embodiment, the amount of movement of the main body 207 to slide toward the distal end side or the proximal end side is not particularly limited, but may be, for example, about several millimeters. In this process, while the hook 62a and the connecting member 3 are engaged, the wire adjusting member 203 is pulled back to the proximal end side together with the operation wire 62 by moving the main body 207 to the proximal end side. As a result, as shown in FIG. 13B, the engaging portion between the hook 62a and the connecting member 3 is pulled into the inside of the sheath 66 and accommodated. The distance between the slider 202 of the operating part 200 and the hook 62*a* changes from the first distance to the second distance. On the other hand, since the operator has not operated the slider 202, the state in which the slider 202 is in contact with the distal end surface 201*a* in the slit 201*b* is maintained.

In the present embodiment, since the operation wire 62 is fixed to the main body 207 of the wire adjusting member 203, even if the operation wire 62 is moved along the axis C1 direction of the main body 207, the length of the operation wire 62 between the main body 207 and the fixing portion 62*b* connected to the hook 62*a* is constant. However, since the main body 207 moves back and forth with respect to the slider 202 of the operating part 200, the operation wire 62 also moves forward and backward with respect to the slider 202. Therefore, according to the wire adjusting member 203 of the present embodiment, the length of the operation wire 62 between the distal end surface of the slider 202 and the fixing portion 62*b* can be adjusted.

Next, the operator releases the compression of the clip case 40 with respect to the compression portion 34, grasps the operating part 100, and removes the insertion portion 60 from the clip case 40. In this process, the operator does not need to pull the slider 202 back to the proximal end side. By this operation, as shown in FIG. 13C, the clip 10 according to the present embodiment can be loaded to the treatment tool main body 30A.

Figure 13C:
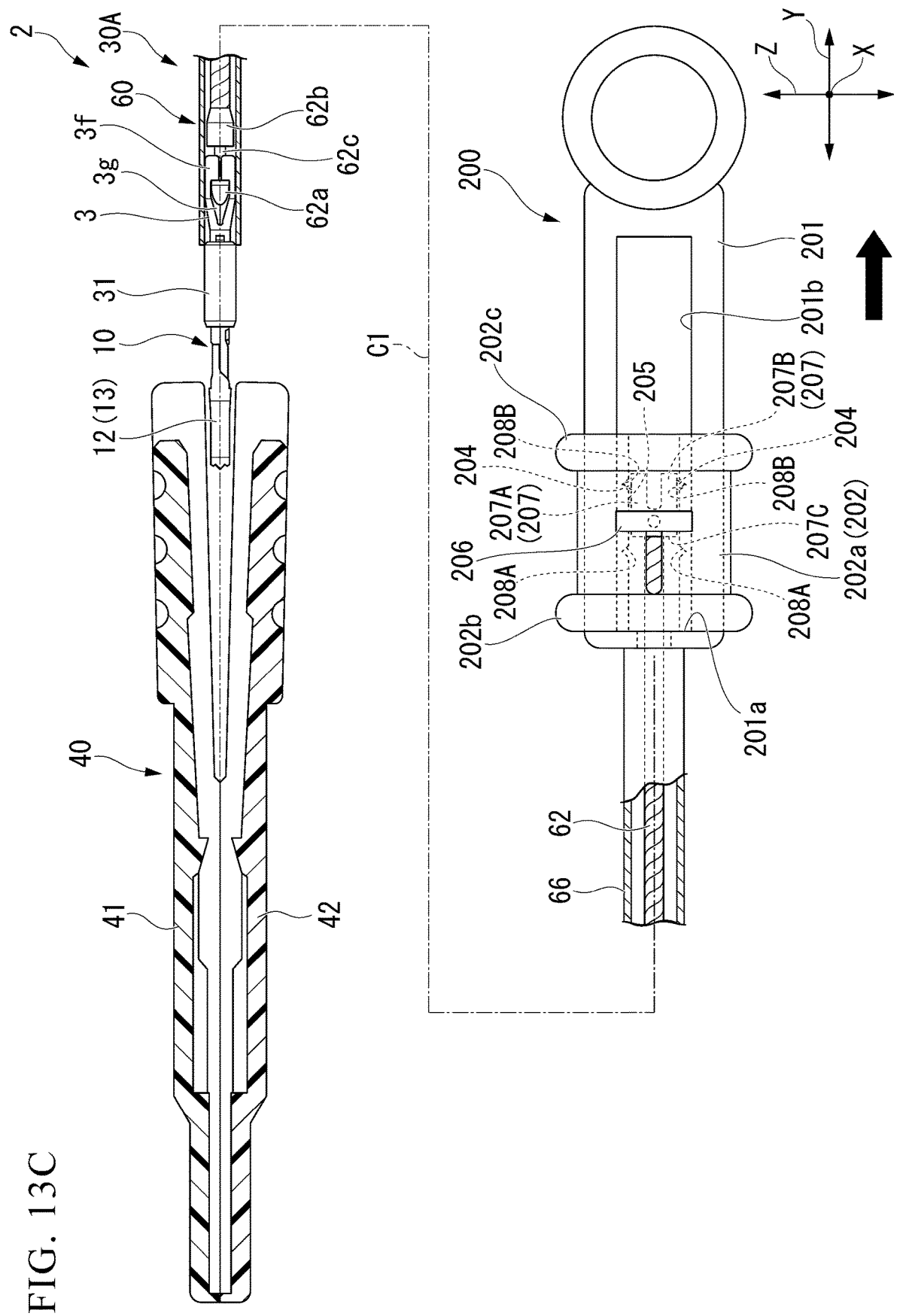
FIG. 13C is a diagram showing an operation of treating a target tissue using the medical apparatus.

At this time, as shown in FIG. 13C, in the operating part 200, the pair of protrusions 204 of the wire adjusting member 203 are engaged in the proximal end recess 208B, and the slider 202 comes into contact with the distal end surface 201*a* in the slit 201*b*. Further, on the distal end side of the medical apparatus 2 removed from the clip case 40, the proximal end surface of the holding tube 31 comes into contact with the distal end surface of the sheath 66.

In the present embodiment, an example in which the pair of tail portions 207A and 207B formed on the main body 207 of the wire adjusting member 203 bends will be described, but the present disclosure is not limited thereto. For example, the pair of protrusions 204 formed on the main body 207 of the wire adjusting member 203 may be made of a material that can be elastically deformed. More specifically, when the operator grasps the knob 206 of the wire adjusting member 203 and moves the main body 207 toward the distal end side along the direction of the axis C1, the pair of tail portions 207A and 207B of the main body 207 do not deform, and the pair of protrusions 204 may be pressed against the inner wall of the cavity 205 of the slider 202 to be elastically deformed and crushed. Then, when the wire adjusting member 203 moves toward the distal end side along the direction of the axis C1 by the operation of the operator, when the pair of protrusions 204 enter the distal end recess 208A, the wire adjusting member 203 may be restored to a conical shape by an elastic restoring force and engaged with the distal end recess 208A.

(Procedure by Medical Apparatus 2)

Hereinafter, a procedure for ligating the target tissue T using the medical apparatus 2 according to the present embodiment having the above configuration will be described with reference to FIGS. 14 to 15C.

When the clip 10 is taken out from the clip case 40 while being loaded to the treatment tool main body 30A, the first arm 12 and the second arm 13 of the arm member 11 of the clip 10 are in an open state in which they are separated from each other. In this state, the operator can guide the medical apparatus 2 to the vicinity of the target tissue T in the body as shown in FIG. 14 by the same operation as in the embodiment described above with respect to FIGS. 1 to 11B.

As shown in FIG. 14, the operator can operate the endoscope, adjust the orientation and orientation of the arm member 11 of the clip 10, and press the arm member 11 toward the target tissue T. At this time, in the operating part 200, the pair of protrusions 204 of the main body 207 of the wire adjusting member 203 engage with the proximal end recess 208B in the cavity 205 of the slider 202, and the state in which the slider 202 is attached to the distal end surface 201*a* of the slit 201*b* is maintained.

In the present embodiment, an example in which the width of the arm member 11 of the clip 10 is appropriate for the size of the target tissue T will be described, but the present disclosure is not limited thereto. When the width of the arm member 11 of the clip 10 is not appropriate for the size of the target tissue T, the operator can appropriately adjust the width of the arm member 11 by operating the slider 202 as in the embodiment described above with respect to FIGS. 1 to 11B.

Figure 15A:
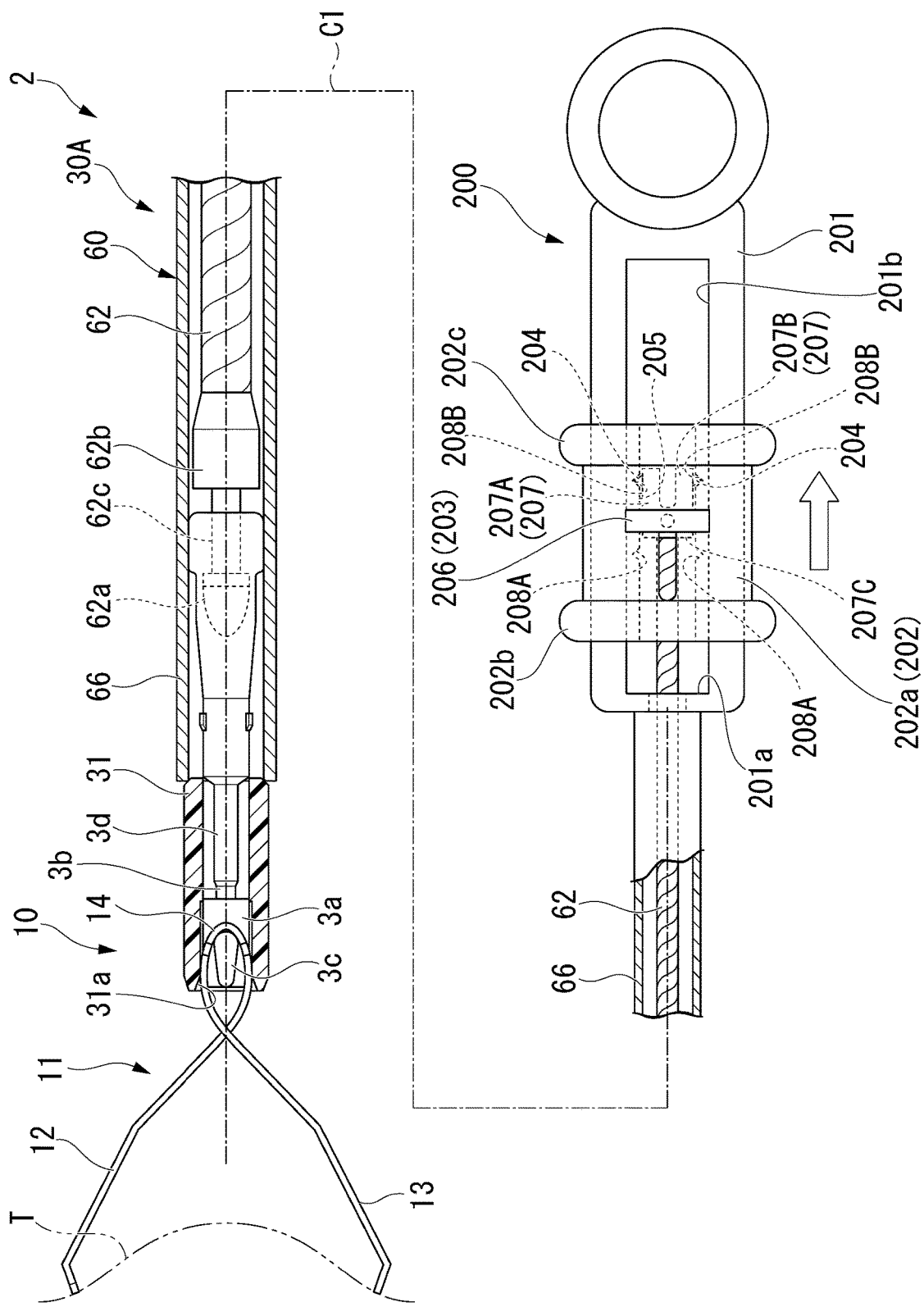
FIG. 15A is a diagram showing an operation of treating a target tissue using the medical apparatus.

After confirming that the target tissue T is positioned between the first arm 12 and the second arm 13, the operator grasps the operating part main body 201 and pulls the slider 202 back to the proximal end side as shown in FIG. 15A. Therefore, the distal end of the first arm 12 and the distal end of the second arm 13 come close to each other, and the opening width of the arm member 11 is reduced. That is, the arm member 11 transitions from the open state to the closed state in a state where the target tissue T is positioned between the first arm 12 and the second arm 13. In this process, since the operator does not operate the wire adjusting member 203, the state in which the pair of protrusions 204 are engaged with the proximal end recess 208B in the cavity 205 of the slider 202 is maintained.

In the present embodiment, as in the embodiment described above with respect to FIGS. 1 to 11B, the operator pushes the slider 202 toward the distal end until the pair of protrusions 16 and 17 provided on the proximal end side of the arm member 11 abut on the stepped portion 31*b* in the holding tube 31. Thereby, the arm member 11 can be moved toward the distal end side. In other words, the arm member 11 can be transitioned to the open state by the operator pushing the slider 202 toward the distal end until the pair of protrusions 16 and 17 on the arm member 11 abut on the stepped portion 31*b*. By this operation, the operator can re-grasp the target tissue T by using the arm member 11. Therefore, in the present embodiment, the operator can repeatedly re-grasp the target tissue T until it can be confirmed that the target tissue T is grasped by the arm member 11 in a desired state.

Figure 15B:
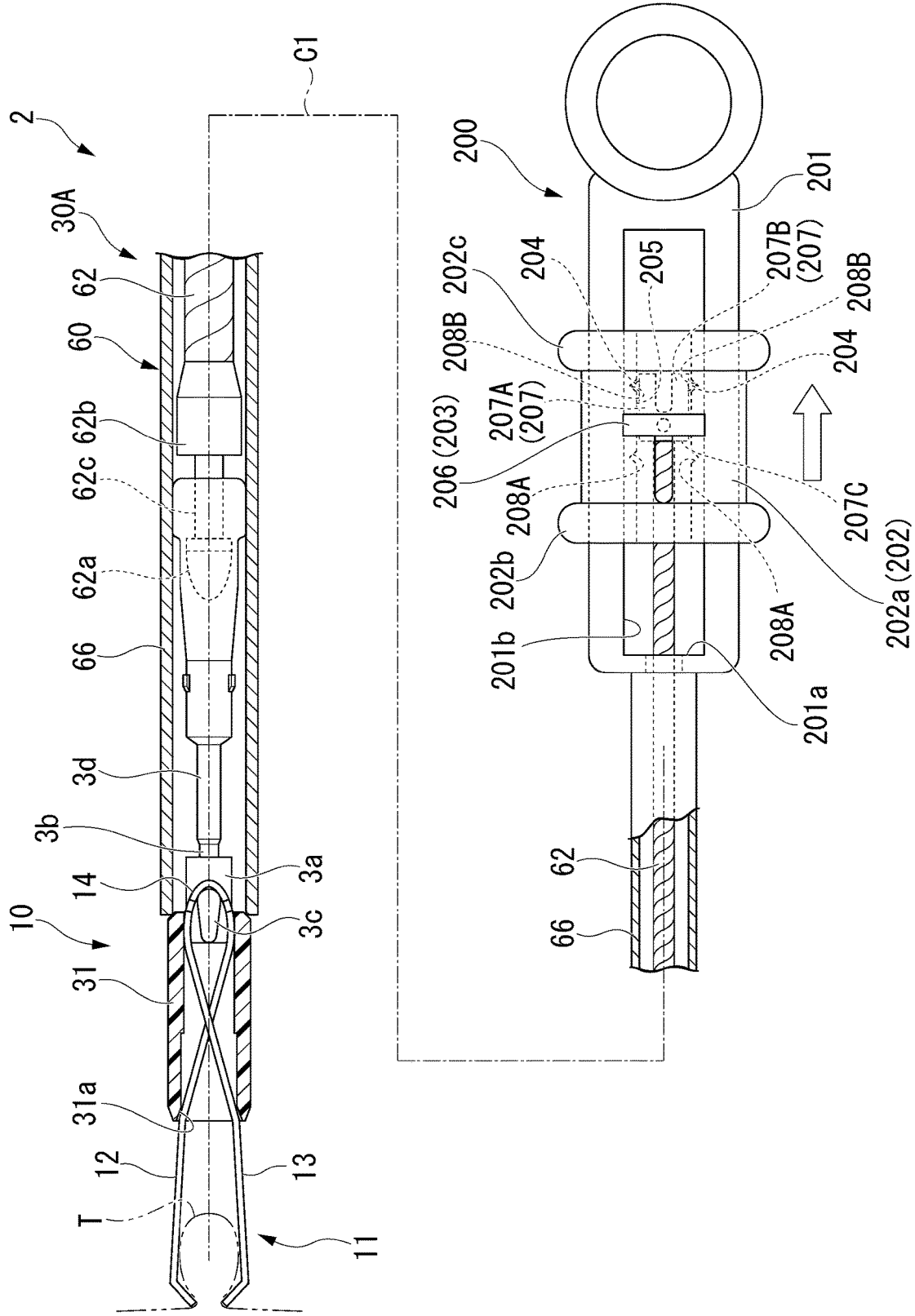
FIG. 15B is a diagram showing an operation of treating a target tissue using the medical apparatus.

When the operator can confirm that the target tissue T is grasped by the arm member 11 in a desired state, the operator pulls the slider 202 in the operating part 200 back to the proximal end side until the pair of protrusions 16 and 17 provided on the proximal end side of the arm member 11 are located on the proximal end side of the opening on the proximal end side of the holding tube 31. By this operation, as shown in FIG. 15B, the target tissue T is held by the first arm 12 and the second arm 13 of the arm member 11 that transitions to the closed state. In this state, the state in which the pair of protrusions 204 are engaged with the proximal end recess 208B in the lumen 205 of the slider 202 is maintained.

At this time, as shown in FIG. 15B, the pair of protrusions 16 and 17 are pulled back to a position protruding from the opening on the proximal end side of the holding tube 31, so that they come into contact with and engage with the proximal end surface of the holding tube 31. That is, even if the operator releases the force for moving the arm member 11 to the proximal end side of the holding tube 31, the stopped state is maintained in which the pair of protrusions 16 and 17 are locked to the distal end side with respect to the proximal end surface of the holding tube 31. The arm member 11 is restricted from moving toward the distal end side with respect to the holding tube 31, and the state of holding the target tissue T in the closed state is locked. In this state, the hook portion 3c hooked on the intermediate portion 14 of the arm member 11 is positioned on the proximal end side of the opening on the proximal end side of the holding tube 31, and is housed in the sheath 66. Further, in this state, the pair of protrusions 16 and 17 of the arm member 11 are locked to the distal end side with respect to the proximal end surface of the holding tube 31, so that the holding tube 31 comes into contact with the sheath 66, but does not press against each other. By operating the slider 202, the operator can move the integrated arm member 11 and the holding tube 31 together with the operation wire 62.

In a state where the target tissue T is bound by the first arm 12 and the second arm 13 of the arm member 11 in the closed state, the operator further pulls the slider 202 further toward the proximal end side. By this operation, as shown in FIG. 15C, when the amount of tensile force in the small diameter portion 3b provided in the connecting member 3 becomes equal to or higher than the predetermined tensile strength of the small diameter portion 3b, the small diameter portion 3b of the connecting member 3 breaks. As a result, the state in which the target tissue T is grasped by the arm member 11 is maintained, and the arm member 11, the holding tube 31, and a part of the connecting member 3 are integrated and placed in the body. The clip 10 to which the target tissue T is ligated is now placed in the body.

After that, the operator operates the endoscope, takes out the medical apparatus 2 from the channel of the endoscope, performs necessary treatment, and completes a series of procedures.

In the present embodiment, when the other clip 10 is reloaded to the treatment tool main body 30A in the medical apparatus 2, the same operation as in the above-described embodiment can be considered. Specifically, the operator first pushes the slider 202 to the most advanced position in the slit 201b, that is, a position in contact with the distal end surface 201a in the slit 201b. Then, the operator does not operate the slider 202, grasps the knob 206 of the wire adjusting member 203, and slides the main body 207 toward the distal end side along the axis C1 direction. As a result, the operator moves the connecting portion between the operation wire 62 and the hook 62a to a position protruding from the opening on the distal end side of the sheath 66 by operating only the wire adjusting member 203 without operating the slider 202.

After that, as in the embodiment described above with respect to FIGS. 1 to 11B, a part of the broken connecting member 3 can be removed from the hook 62a by the operations shown in FIGS. 7A and 7B. The operator can sterilize the treatment tool main body 30A as needed, and load another clip 10 to the treatment tool main body 30A in the same manner as described above.

(Effect of Medical Apparatus 2)

According to the medical apparatus 2 of the present embodiment, as in the medical apparatus 1 of the embodiment described above, the operator does not operate the slider 202, and by moving the main body 207 of the wire adjusting member 203 forward and backward with respect to the slider 202, the distance between the slider 202 and the hook 62a can be adjusted to the first distance and the second distance. However, according to the medical apparatus 2 of the present embodiment, even if the operator operates the wire adjusting member 203, the length of the operation wire from the position where the operation wire 62 is fixed to the main body 207 of the wire adjusting member 203 to the fixing portion 62b connected to the hook 62a is constant.

According to the medical apparatus 2 of the present embodiment, similarly to the medical apparatus 1 of the embodiment described above, with respect to the treatment tool main body 30A, both the reloadable operation of the clip 10 and the re-grasping operation of the target tissue T using the clip 10 can be achieved at the same time.

While preferred embodiments have been described and illustrated above, it should be understood that these are exemplary and are not to be considered as limiting. Additions, omissions, substitutions, and other modifications can be made without departing from the spirit or scope of the present disclosure. Accordingly, the disclosure is not to be considered as being limited by the foregoing description, and is only limited by the scope of the appended claims.

According to each of the above-described embodiments of the present disclosure, it is possible to provide a medical apparatus and an applicator capable of achieving both reloadability of the treatment tool and re-grasping operation of the target tissue by the treatment tool. Further, in this medical apparatus, it is also possible to provide a method of suitably loading the treatment tool to the medical apparatus by engaging the treatment tool with the applicator.

What is claimed is:

1. An applicator comprising:
   a link capable of engaging with a clip unit;
   an operation wire that is connected to the link;
   a sheath capable of accommodating the link;
   a slider that is configured to be operated to advance and retract the operation wire; and
   a knob that is configured to adjust a length of the operation wire, the knob being provided in the slider,
   wherein, in a state where the slider is in an advanced-most position, the knob is configured to adjust the length of the operation wire between:
      a first length at which the link protrudes from the sheath, and
      a second length at which the link is positioned inside the sheath, the second length being shorter than the first length.

2. The applicator according to claim 1, further comprising a restricting button that is configured to restrict operation of the knob to adjust the length of the operation wire.

3. The applicator according to claim 1, wherein:
   the knob includes a rotatable shaft, and
   the operation wire is configured to wind around or unwind from the rotatable shaft by a rotational movement of the rotatable shaft when the knob is operated to adjust the length of the operation wire.

4. The applicator according to claim 3, further comprising a restricting button that is configured to restrict the rotational movement of the rotatable shaft to adjust the length of the operation wire.

5. The applicator according to claim 1, wherein:
   the knob includes a slidable main body that is movably engaged with the slider, and
   the operation wire is fixed to the slidable main body of the knob.

6. The applicator according to claim 5, wherein:
   the knob is configured to be operated to advance or retract the slidable main body with respect to the slider to adjust the length of the operation wire between the first length and the second length, and the slidable main body includes a protrusion that is configured to lock to the slider at a position where the length of the operation wire is the second length.

7. A medical apparatus, comprising:

a clip unit including a first arm, a second arm, and a first link; and an applicator capable of operating the clip unit, the applicator including:

a second link capable of engaging with the first link;

an operation wire that is configured to advance and retract the second link;

a sheath capable of accommodating the second link so that engagement between the first link and the second link cannot be disengaged;

a slider that is connected to the operation wire and is configured to be operated to advance and retract the second link; and a knob that is configured to adjust a length of the operation wire extending from the slider to the second link, the knob including a rotatable shaft, wherein the operation wire is configured to wind around or unwind from the rotatable shaft by a rotational movement of the rotatable shaft when the knob is operated to adjust the length of the operation wire, and wherein, in a state where the slider is in an advanced-most position at which the slider cannot be operated to further advance the second link, the knob is configured to adjust the length of the operation wire extending from the slider to the second link between:

a first length at which the second link protrudes from the sheath, and a second length at which the second link is positioned inside the sheath, the second length being shorter than the first length.

8. The medical apparatus according to claim 7, wherein:

the clip unit is formed in a tubular shape and includes a holding tube into which the first arm and the second arm can be inserted, and the first link is connected to the first arm and the second arm, and is arranged at a position protruding from the holding tube.

9. The medical apparatus according to claim 7, wherein the applicator further includes a restricting button that is configured to restrict operation of the knob to adjust the length of the operation wire extending from the slider to the second link.

10. The medical apparatus according to claim 7, wherein the applicator further includes a restricting button that is configured to restrict the rotational movement of the rotatable shaft to adjust the length of the operation wire extending from the slider to the second link.

11. The medical apparatus according to claim 7, wherein:

the knob includes a slidable main body that is movably engaged with the slider, and the operation wire is fixed to the slidable main body of the knob.

12. The medical apparatus according to claim 11, wherein:

the knob is configured to be operated to advance or retract the slidable main body with respect to the slider to adjust the length of the operation wire extending from the slider to the second link between the first length and the second length, and the slidable main body includes a protrusion that is configured to lock to the slider at a position where the length of the operation wire extending from the slider to the second link is the second length.

13. The medical apparatus according to claim 7, wherein the knob is provided in the slider.

14. A method for operating a medical apparatus comprising a clip unit including a first link, and an applicator that is capable of operating the clip unit and includes a second link capable of engaging with the first link of the clip unit, and an operation wire that is configured to advance and retract the second link, the method comprising:

advancing the second link of the applicator by operating a slider of the applicator to an advanced-most position at which the slider cannot be operated to further advance the second link;

adjusting a length of the operation wire extending from the slider to the second link to a first length by operating a knob of the applicator, the knob being configured to adjust the length of the operation wire extending from the slider to the second link between the first length and a second length that is shorter than the first length in a state where the slider is in the advanced-most position; and engaging and/or disengaging the first link of the clip unit and the second link of the applicator in a state where the slider is in the advanced-most position and the length of the operation wire extending from the slider to the second link is the first length, wherein the length of the operation wire extending from the slider to the second link is adjusted by operating the knob to wind or unwind the operation wire around a rotatable shaft of the knob.

* * * * *